United States Patent
Satake et al.

(10) Patent No.: US 9,687,143 B2
(45) Date of Patent: Jun. 27, 2017

(54) OPHTHALMIC PHOTOGRAPHY DEVICE, OPHTHALMIC PHOTOGRAPHY METHOD, AND OPHTHALMIC PHOTOGRAPHY PROGRAM

(71) Applicant: NIDEK CO., LTD., Gamagori, Aichi (JP)

(72) Inventors: Norimasa Satake, Nukata-gun (JP); Tetsuya Kanou, Toyota (JP)

(73) Assignee: NIDEK CO., LTD., Gamagori (JP)

( * ) Notice: Subject to any disclaimer, the term of this patent is extended or adjusted under 35 U.S.C. 154(b) by 124 days.

(21) Appl. No.: 14/671,636

(22) Filed: Mar. 27, 2015

(65) Prior Publication Data

US 2015/0272432 A1    Oct. 1, 2015

(30) Foreign Application Priority Data

Mar. 31, 2014  (JP) ................. 2014-073656

(51) Int. Cl.
| | |
|---|---|
| A61B 3/14 | (2006.01) |
| A61B 3/00 | (2006.01) |
| A61B 3/18 | (2006.01) |
| A61B 3/12 | (2006.01) |
| A61B 3/10 | (2006.01) |
| A61B 3/113 | (2006.01) |

(52) U.S. Cl.
CPC ............ *A61B 3/0025* (2013.01); *A61B 3/18* (2013.01); *A61B 3/102* (2013.01); *A61B 3/113* (2013.01); *A61B 3/12* (2013.01); *A61B 3/14* (2013.01)

(58) Field of Classification Search
CPC .. A61B 3/14; A61B 3/12; A61B 3/103; A61B 3/1015; A61B 3/113; G06F 3/013
USPC .......... 351/205, 206, 209, 210, 246
See application file for complete search history.

(56) References Cited

U.S. PATENT DOCUMENTS

2007/0129709 A1* 6/2007 Andersen et al. ........... 606/4
2009/0180073 A1* 7/2009 Ichikawa et al. ........ 351/208
2010/0103374 A1* 4/2010 Hirose et al. ............ 351/206

FOREIGN PATENT DOCUMENTS

EP        1952755 A1 *  8/2008
JP     2013056274 A     3/2013

* cited by examiner

*Primary Examiner* — James Greece
(74) *Attorney, Agent, or Firm* — Oliff PLC

(57) ABSTRACT

Disclosed is an ophthalmic photography device for capturing an eye including: a first photography optical system that captures a first image of the eye by capturing the eye by performing a first type of photography; a second photography optical system that captures a second image of the eye by capturing the eye by performing a second type of photography; a third photography optical system that captures a front image of the eye by capturing the eye using a third type of photography; and a controller for acquiring a first front image when the first image is acquired, and acquiring a second front image different from the first front image when the second image is acquired; and for detecting the amount of positional deviation between the first and second front images, and correlating the first image to the second image based on the amount of positional deviation.

12 Claims, 6 Drawing Sheets

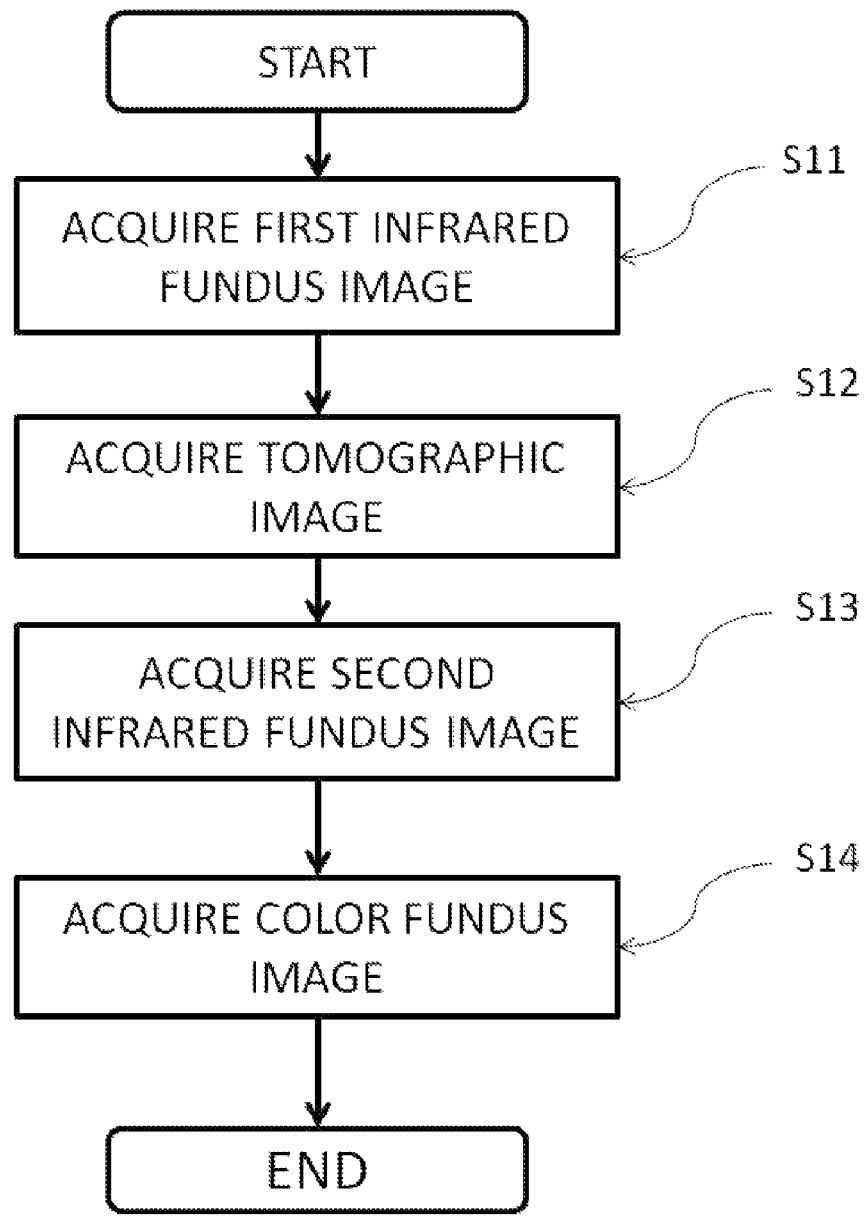

OPHTHALMIC PHOTOGRAPHY DEVICE, OPHTHALMIC PHOTOGRAPHY METHOD, AND OPHTHALMIC PHOTOGRAPHY PROGRAM

CROSS REFERENCE TO RELATED APPLICATION

This application is based upon and claims the benefit of priority of Japanese Patent Application No. 2014-073656 filed on Mar. 31, 2014, the contents of which are incorporated herein by reference in its entirety.

BACKGROUND

The present invention relates to an ophthalmic photography device for capturing a subject's eye, an ophthalmic photography method, and an ophthalmic photography program.

BACKGROUND ART

In the related art, there is known an optical coherence tomography (OCT) using low-coherent light as an ophthalmic device that can non-invasively capture a tomographic image of a subject's eye.

A compound device of the OCT and a fundus camera is proposed as a device using the OCT (refer to JP-A-2013-056274). For example, in this compound device, the analysis result of a correlation between a tomographic image captured using the OCT and a fundus image (a front image of a fundus) captured by the fundus camera is displayed on a display unit. Accordingly, an inspector can confirm which portion of the fundus image acquired by the fundus camera is captured as the tomographic image acquired using the OCT. For example, the correlation between the tomographic image acquired using the OCT and the fundus image acquired by the fundus camera is performed by acquiring an OCT front image from a coherence signal acquired using the OCT, and matching the acquired OCT front image with the fundus image (the front image of the fundus) captured by the fundus camera.

When the front images used as references for a correlation between different images are captured by different methods, it may be difficult to correlate the different images due to distortion caused by an optical system, a difference in the photographic angle of view and contrast, or the like. Accordingly, a correlation between the different images may not be accurately performed.

SUMMARY

The present invention is made in light of this problem, and an object of the present invention is to provide an ophthalmic photography device, an ophthalmic photography method, and an ophthalmic photography program by which it is possible to accurately perform a correlation between images.

The present invention has the following configuration so as to achieve the object.

An ophthalmic photography device for capturing a subject's eye, the device comprising:

a first photography optical system configured to capture a first image of the subject's eye by performing a first type of photography;

a second photography optical system configured to capture a second image of the subject's eye by performing a second type of photography that is different from the first type of photography;

a third photography optical system configured to capture a front image of the subject's eye by performing a third type of photography that is different from the first and second types of photography; and a controller configured to: (i) control the third photography optical system to capture a first front image when the first image is captured by the first photography optical system, and to capture a second front image different from the first front image when the second image is captured by the second photography optical system, (ii) detect an amount of positional deviation between the first front image and the second front image, and (iii) associate the first image with the second image based on the amount of positional deviation.

An ophthalmic image processing method comprising:

capturing a first image of a subject's eye by performing a first type of photography;

capturing a second image of the subject's eye by performing a second type of photography that is different from the first type of photography;

capturing a front image of the subject's eye by performing a third type of photography that is different from the first and second types of photography, the capturing of the front image including capturing a first front image with the third type of photography when the first image is captured, and capturing a second front image with the third type of photography when the second image is captured, the second front image being different from the first front image; and detecting an amount of positional deviation between the first front image and the second front image, and associating the first image with the second image based on the amount of positional deviation.

BRIEF DESCRIPTION OF THE DRAWINGS

FIG. 7 is a flowchart illustrating an example of a photographic operation according to the embodiment.

DESCRIPTION OF ILLUSTRATIVE EMBODIMENTS

Figure 1A:
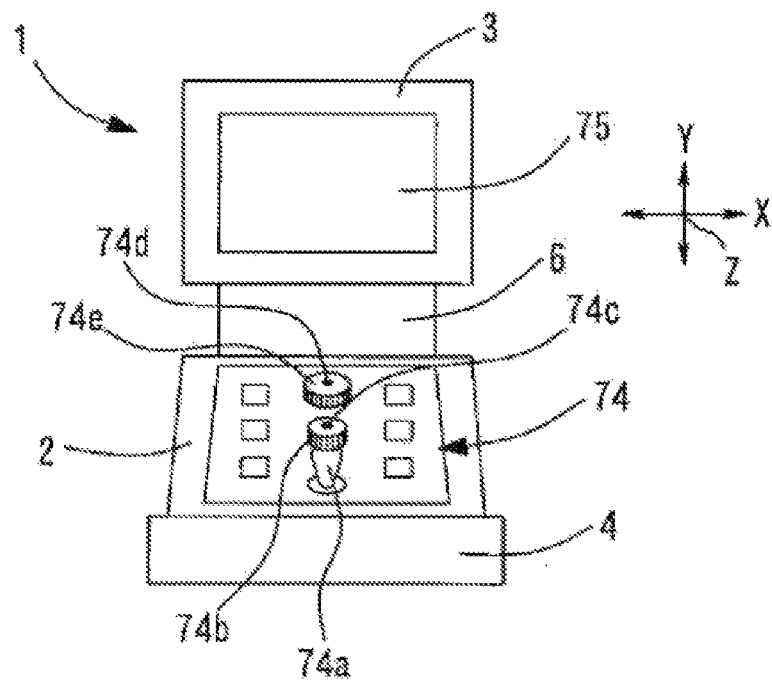
FIGS. 1A and 1B show schematic views illustrating the exterior of a fundus photography device according to an embodiment.

A typical embodiment of the present invention will be described with reference to the accompanying drawings. In the following description of the embodiment, a Z direction (a direction of an optical axis L1) refers to a direction of the depth of a subject's eye, an X direction refers to a horizontal component on a plane (a plane being flush with a subject's face) perpendicular to the direction of the depth, and a Y direction refers to a vertical component on the plane.

A device 1 mainly includes a coherence optical system (an OCT optical system) 200; a fundus illumination optical system (hereinafter, may be referred to as an illumination optical system) 10; a fundus photography optical system (hereinafter, may be referred to as a photography optical system) 30; and a control unit (for example, a PC 90 and a control unit 70) (refer to FIG. 2). An optical axis L2 of the coherence optical system 200 is disposed coaxially with an optical axis L1 of the fundus illumination optical system 10 and the fundus photography optical system 30 by using an optical path division member. Naturally, the optical axis L1 may not coaxial with the optical axis L2.

<OCT>

The coherence optical system 200 may be provided so as to obtain a tomographic image of a fundus Ef of a subject's eye using optical coherence tomography. The coherence optical system 200 includes a splitter (a light divider); light scanning unit; and light detector (a photodetector).

The splitter (for example, a coupler 104) may be provided so as to divide light from an OCT light source (for example, a measurement light source 102) into light via a measurement optical path and light via a reference optical path. The measurement light path (for example, a fiber system or a lens system) may be configured to guide measurement light to the fundus Ef. The reference optical path may be configured to advance reference light in the device and to induce coherence between the reference light and the measurement light.

The light scanning unit (for example, the scanning unit 108) may be provided so as to scan the measurement light on the fundus Ef. For example, the light scanning unit may be disposed on the measurement light path, and scan the measurement light to be illuminated on the fundus of the subject's eye via the measurement light path.

The light detector (for example, a detector 120) may be provided so as to detect light that is obtained by combining fundus-reflected light produced by the measurement light from the measurement light path and the light from the reference optical path. A combiner may combine the measurement light from the measurement optical path reflected by the fundus Ef and the reference light from the reference optical path. A beam splitter, a half mirror, a fiber coupler, a circulator, or the like is used as the splitter and the combiner.

The control unit (for example, the PC 90 and the control unit 70) as an OCT image acquisition unit may control the light scanning unit to scan the measurement light, and acquire at least a tomographic image of the fundus Ef based on an output signal from the light detector. In addition, the control unit may control the light scanning unit to scan the measurement light, and acquire a tomographic image of the fundus Ef based on an output signal from the light detector, and a first front image (for example, an OCT front image 84) (a front observation image) based on an output signal from the light detector.

In regard to the acquisition of a tomographic image, for example, the control unit may control the light scanning unit to scan the measurement in a vertical direction, and acquire a tomographic image of the fundus Ef based on an output signal from the light detector. The control unit may control the light scanning unit and acquire a tomographic image corresponding to a scanning position set in response to an operation signal generated by an inspector, or the control unit may control the light scanning unit and acquire a tomographic image corresponding to a scanning position stored in a storage unit (for example, a memory 72). The scanning position may be changed vertically and laterally with respect to the fundus Ef, or may be changed in a rotation direction with respect to the fundus Ef.

In addition, the control unit may control the light scanning unit and acquire a tomographic image corresponding to a scanning pattern set in response to an operation signal generated by an inspector, or the control unit may control the light scanning unit and acquire a tomographic image corresponding to a scanning pattern stored in the storage unit. The scanning pattern may be a line scan or a circle scan. A cross scan, a radial scan, a multiple line scan, a raster scan (a map scan), and the like are examples of the scanning pattern in which a plurality of different scanning lines are arrayed.

In regard to the acquisition of the first front image, the control unit may control the light scanning unit to scan the measurement light in two dimensions (for example, raster scan), and acquire the first front image (for example, the OCT front image 84) (front observation image) of the fundus Ef based on an output signal from the light detector.

For example, the control unit may acquire the first front image based on the phase of a spectroscopic signal at each X-Y position. At this time, the control unit may generate the first front image based on the number of zero cross points of a coherence signal (for example, refer to JP-A-2011-215134). The control unit 70 may acquire the first front image based on the intensity of a spectroscopic signal at each X-Y position.

For example, after the control unit generates three-dimensional OCT data based on a spectroscopic signal at each position, the control unit may generate the first front image based on the three-dimensional OCT data. At this time, the control unit may acquire the first front image by integrating signal intensity distributions (distributions in a direction of the depth of the subject's eye) of the three-dimensional OCT data at the X-Y positions. The first front image may be a retina outer layer OCT image, or may be a C scan image indicative of a signal intensity distribution at a constant depth position. The first front image is not limited to the above-mentioned images, and may be a fundus observation image obtained by performing a specific analysis process of a detection signal from the light detector.

The acquired first front image may be displayed in a live mode on the display unit. At this time, the control unit may alternately acquire the first front image and a first tomography image corresponding to a set scanning pattern by controlling the light scanning unit. At this time, the first front image and the tomographic image may be alternately acquired once at a time. Alternatively, the first front images are acquired multiple times, and then the first tomographic image (one first tomographic image or a plurality of the first tomographic images) may be acquired. At least one first front image may be acquired, and then a plurality of the first tomographic images may be acquired.

It is possible to acquire a high-resolution tomographic image by setting a scanning speed during the acquisition of the tomographic image to be higher than that during the acquisition of the front image. The tomographic image may be extracted from the three-dimensional OCT data used as an original data of the first front image, and may be displayed.

The first front image as a live image may be an image (for example, an added average image) obtained by combining a plurality of the first front consecutive images. The control unit may perform a scan multiple times at each position, and acquire the first front image based on a plurality of spectroscopic signals. The tomographic image may also be displayed in a live mode on the display unit.

The control unit may acquire the first front image by controlling the light scanning unit, and acquire the tomographic image corresponding to measurement positions set on the first front image displayed on the display unit.

<FC>

The fundus illumination optical system 10 may be provided so as to simultaneously illuminte a two-dimensional region on the fundus Ef by illumination light. At this time, the fundus illumination optical system 10 includes a photography light source 14 and an observation light source 11, and may simultaneously illuminate the two-dimensional region on the fundus Ef by illumination light from at least either one of the photography light source 14 and the observation light source 11. The photography light source 14 and the observation light source 11 may be separate light sources, or may be the same light source.

For example, the illumination optical system 10 may be provided so as to illuminate the fundus Ef by the illumination light via a mirror portion 22b of a hole mirror and an objective lens 25. The illumination light may be at least either one of the visible light and the infrared light. The infrared light is preferably used as the illumination light so as to prevent an occurrence of mydriasis, and the illumination optical system 10 may include a visible light illumination optical system that illuminates the fundus Ef by the visible light, and an infrared light illumination optical system that illuminates the fundus Ef by the infrared light.

The fundus photography optical system 30 may be provided so as to capture a front image of the fundus Ef illuminated by the illumination light using a two-dimensional imaging element. In this case, the fundus photography optical system 30 may include a (first) two-dimensional imaging element 35 that captures the fundus, and a (second) two-dimensional imaging element 38 for observing the fundus, and may capture a front image of the fundus Ef illuminated by the illumination light. The imaging element for photography and the imaging element for observation may be respectively formed of different imaging elements, or may be formed of the same imaging element. The imaging elements may be disposed conjugately with the fundus.

The fundus photography optical system 30 may be provided so as to capture a front image of the fundus Ef illuminated by the illumination light of the illumination optical system 10 via an opening 22a of a hole mirror 22. The fundus photography optical system 30 may include a focusing lens 32 that can move in an optical axis direction.

The fundus photography optical system 30 may include a (first) imaging element (for example, the two-dimensional imaging element 35) that captures a still image of the fundus, and a second imaging element (for example, the two-dimensional imaging element 38) for observing the fundus in a moving picture mode. The imaging element for photography and the imaging element for observation may be respectively formed of different imaging elements, or may be formed of the same imaging element. The fundus illumination optical system 10 and the fundus photography optical system 30 may form a fundus camera optical system 100 that captures the fundus of the subject's eye.

<Display (for Example, Refer to FIG. 3) of First Front Image (for Example, OCT Front Image 84) and Second Front Image (for Example, FC Front Image 92)>

The control unit (for example, the PC 90 and the control unit 70) may be used as display control unit. The display control unit controls a display of the display unit (for example, a display unit 75 and a display unit 95). At this time, for example, the display control unit may simultaneously display the first front image and a second front image in different display regions. Here, the first front image is based on the output signal from the light detector of the coherence optical system 200, and the second front image is a front observation image of the fundus Ef based on an imaging signal from the two-dimensional imaging element of the fundus photography optical system 30 (refer to FIG. 3).

Accordingly, it is possible to properly adjust the coherence optical system 200 using the first front image and the fundus illumination optical system 10 or the fundus photography optical system 30 using the second front image. The adjustment of the coherence optical system 200 may be the adjustment of a scanning position, the adjustment of the position of a fixation lamp, the adjustment of a focus, the control of a polarized wave, or the like. The adjustment of the fundus illumination optical system 10 or the fundus photography optical system 30 may be the adjustment of alignment or a focus with respect to the subject's eye. As a result, it is possible to smoothly capture a good tomographic image and a good fundus front image (for example, a color fundus image or a fluorescent fundus image).

The first front image and the second front image are preferably displayed as live images. The inspector can easily understand a state of the subject's eye or the device while watching the live images.

The display control unit may simultaneously display the first front image and the second front image in different display regions. Here, the first front image is based on the output signal from the light detector of the coherence optical system 200, and the second front image is a front observation image of the fundus Ef based on the imaging signal from the (second) two-dimensional imaging element 38 for observing the fundus.

Figure 3:
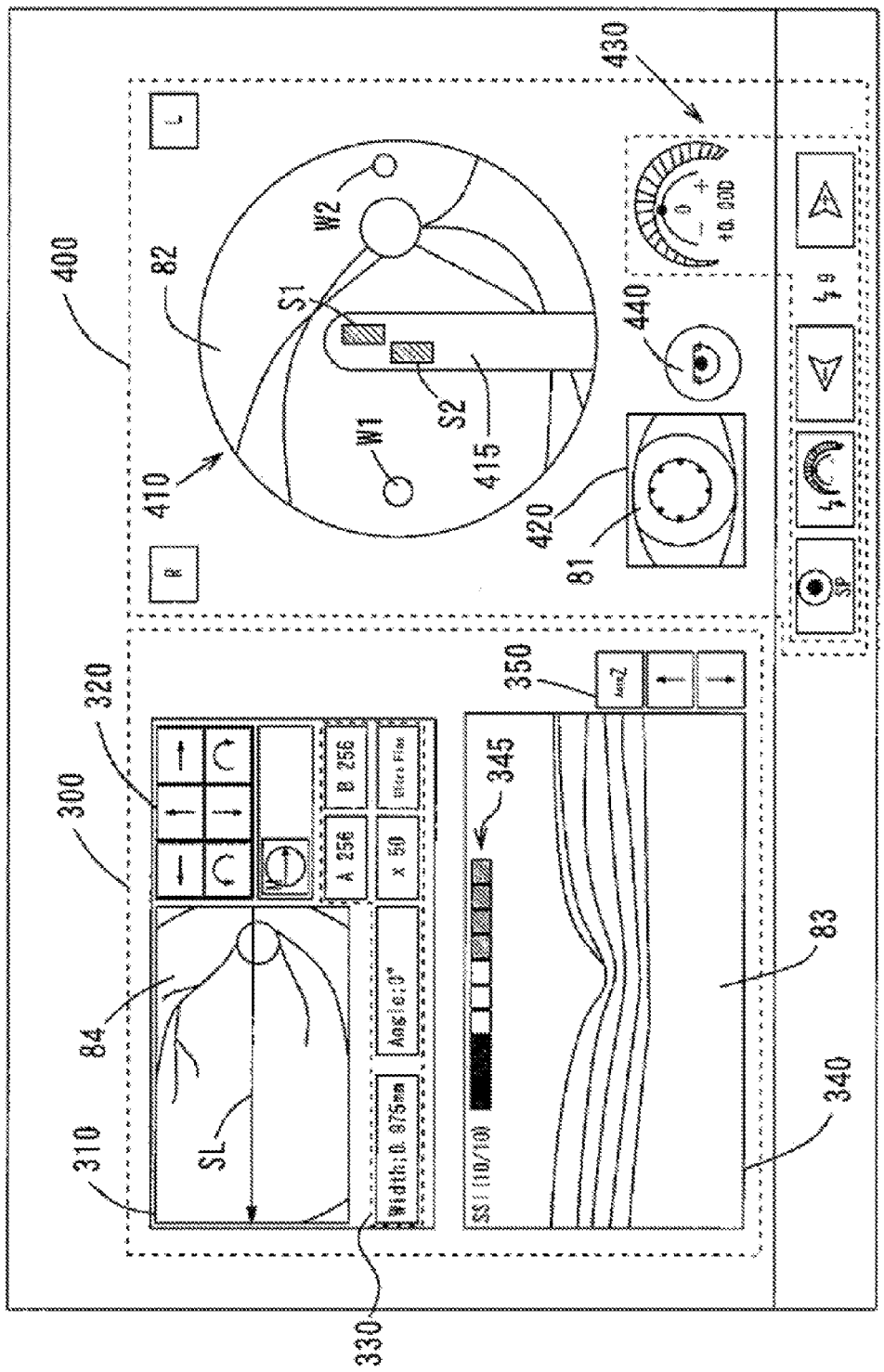
FIG. 3 is a view illustrating an example of a screen displayed on a display unit according to the embodiment.

When the first front image and the second front image are simultaneously displayed in different display regions, the display control unit may display the first front image and the second front image in different regions on a display screen of the same display unit (refer to FIG. 3). At this time, for example, the display control unit may display the first front image in a first display region on the display unit, and display the second front image in a second display region different from the first display region. The first front image and the second front image may be displayed vertically or laterally side by side. The first front image and the second front image may be displayed while being separated from each other. The first front image and the second front image may be displayed in different sizes, or may be displayed in the same size. In the following example, the second front image is displayed at a display magnification higher than that of the first front image. Accordingly, the inspector can easily confirm states such as a flare and non-homogeneous illumination. Naturally, the first front image is displayed at a display magnification higher than that of the second front image. Accordingly, the inspector can easily confirm a passage state of a blood vessel, an abnormal portion, and the like. In regard to the display of the first front image and the second front image, a display magnification may be set based on a photographic angle of view. That is, a display magnification may be set corresponding to a photographic angle of view of an optical system. For example, when the angle of view of the first front image is 30 degrees, and the angle of view of the second front image is 45 degrees, the second front image may be displayed at a display size 1.5 times that of the first front image.

For example, the display control unit may display the first front image on one (for example, the display unit 95) of a plurality of the display units, and the second front image on the other (for example, the display unit 75) of the plurality of display units.

At least a part of the captured fundus Ef may be displayed on both the first front image and the second front image (refer to FIG. 3). At this time, when the optical axis of the coherence optical system 200 is disposed coaxially with the optical axis of the fundus illumination optical system 10 and the fundus photography optical system 30, a imaging regions in the vicinity of the optical axes is set as at least the same imaging region.

The display control unit may be able to superimpose the second front image on the first front image, or may be able to superimpose the first front image on the second front image. For example, in a state where the first front image and the second front image are displayed in different display regions, at least one front image is displayed while being superimposed by the other front image.

The display control unit may divisively display the first display region (for example, a display region 300) in which images acquired by the coherence optical system 200 are integrally displayed, and the second display region (for example, a display region 400) in images acquired by the fundus illumination optical system 10 and the fundus photography optical system 30 are integrally displayed (refer to FIG. 3).

Accordingly, since a display related to the OCT and a display related to the fundus front image photography (for example, fundus camera) are divisively displayed, the inspector can smoothly set various conditions.

For example, the first display region may be provided on a left side in the display unit, and the second display region may be provided on a right side in the display unit. The first display region and the second display region may be respectively provided on the right and left sides, or may be divided vertically.

The first display region may display a tomographic image and photographic conditions related to the coherence optical system in addition to the first front image. An example of the photographic conditions related to the coherence optical system 200 may be a scanning position of the light scanning unit. The scanning position may be changed based on an operation signal from an operation unit. The display region may be provided so as to change an optical path difference between the measurement light and the reference light, and the optical path difference may be adjusted based on an operation signal input via the display region.

The second display region may display photographic conditions related to at least either one of the fundus illumination optical system 10 and the fundus photography optical system 20 in addition to the second front image. The photographic conditions may include at least any one of the following variables: the position of the focusing lens; the amount of photography light emitted from the photography light source 14; a selection between a short exposure photography mode and a normal exposure photography mode; a selection between a small-pupil photography mode and a normal-pupil photography mode; and the like.

The display unit may be a touch panel, or the photographic conditions may be changed based on an operation signal input via the touch panel. Naturally, the display unit is not limited to the touch panel, and the photographic conditions may be changed based on a scanning signal displayed on the display unit via an interface such as a mouse or a keyboard.

<Display of Index on Second Front Image>

The device 1 may be provided with an index projection optical system that projects an index on the subject's eye. The index projection optical system may be at least any one of the following index projection optical systems: an index projection optical system (for example, a focus index projection optical system 40) that projects a focus index (for example, a split index) on the fundus of the subject's eye; an index projection optical system (for example, an infrared light source 55) that projects an alignment index on the subject's eye; and an index projection optical system that projects a fixation target on the subject's eye.

Light emitted from the index projection optical system and reflected by the subject's eye may be imaged by the two-dimensional imaging element (for example, the two-dimensional imaging element 38) of the fundus photography optical system 30. At this time, the display control unit may display indexes (for example, S1, S2, W1, and W2) on the second front image based on an imaging signal from the two-dimensional imaging element. A technique of displaying an index may be at least any one of the following techniques: a technique of directly displaying an imaged index; a technique of superimposing an electronic display (for example, a colored display) on an index; a display of an indicator based on a result of detection of an index position.

<Display of Scanning Line on First Front Image>

The display control unit may electronically display a scanning line (for example, a scanning line SL) on the first front image, the scanning line being indicative of a measurement position of a tomographic image displayed on the display unit. Accordingly, it is possible to set a scanning position using the OCT front image on which it is easy to confirm a state of blood vessels or an abnormal portion.

The scanning line may move based on an operation signal from the operation unit operated by the inspector. The control unit may acquire a tomographic image corresponding to the scanning position moved by the inspector. The display control unit may not electronically display the scanning line on the second front image.

The display control unit may display an index on the second front image based on an imaging signal from the two-dimensional imaging element, and electronically display a scanning line on the first front image, the scanning line being indicative of a measurement position of a tomographic image displayed on the display unit. Accordingly, the index (for example, the focus index, the alignment index, or the fixation target) displayed on the second front image is not superimposed on the scanning line, and thereby it is possible to easily perform various adjustments.

<Display of Anterior Chamber Image>

The device 1 may be provided with an anterior chamber observation optical system 60 for observing an anterior chamber image of the subject's eye. The display control unit may simultaneously display an anterior chamber image acquired by the anterior chamber observation optical system 60, a tomographic image, the first front image, and the second front image.

<Modifications>

As described above, the device 1 may be provided with the index projection optical system that projects the index (for example, the focus index or the alignment index) on the subject's eye. At this time, the display control unit may display a first front observation image of the fundus Ef based on an output signal from the light detector or an imaging signal from the two-dimensional imaging element of the fundus photography optical system 30, the first front observation image containing a scanning line indicative of a measurement position of a tomographic image displayed on the display unit. In addition, the display control unit may display a second front observation image of the fundus Ef based on an imaging signal from the two-dimensional imaging element of the fundus photography optical system 30, the second front observation image containing an index based on the imaging signal from the two-dimensional imaging element. The display control unit may simultaneously display the first front observation image and the second front observation image in different display regions.

Accordingly, the displayed scanning line is not superimposed on the second front observation image containing the index, and thereby it is possible to easily performs an adjustment using the index. At this time, the index may be displayed on the first front observation image. The reason is that the first front observation image is mainly used to set a scanning position, and it does not comparatively matter whether the index is present.

The first front observation image and the second front observation image may be acquired by the same optical system and imaging element, or may be acquired by separate optical systems.

When the first front observation image and the second front observation image may be acquired by the same optical system and imaging element, the control unit may control the index projection optical system (for example, a light source 41 or the light source 55) to turn an index on and off. At this time, the display control unit may acquire a front observation image at the turning off of the index as the first observation image and display the front observation image on the display unit, and acquire a front observation image at the turning on of the index as the second observation image and display the front observation image on the display unit.

<Others>

The application of this control is not limited to the above-mentioned optical systems in the embodiment, and this control can be applied to other optical systems. For example, the fundus illumination optical system 10 may be an optical system that illuminates the fundus of the subject's eye by illumination light. The fundus photography optical system 30 may be an optical system that captures a front image of the fundus illuminated by the illumination light using the photodetector.

As described above, the fundus illumination optical system 10 and the fundus photography optical system 30 may be configured to simultaneously illuminate the two-dimensional region of the fundus, and to capture a front image of the fundus using the photodetector (for example, the two-dimensional imaging element). Each of the fundus illumination optical system 10 and the fundus photography optical system 30 may be an SLO. The SLO can capture a front image of the fundus by scanning a laser beam on the fundus and receiving reflected light using a photodetector (for example, a point sensor).

At this time, the display control unit may simultaneously display the first front image and the second front image in different display regions. Here, the first front image is based on an output signal from the light detector, and the second front image is a front observation image of the fundus Ef based on a photodetection signal from the photodetector. Naturally, each of the above-mentioned technologies can also be applied to this configuration.

Accordingly, it is possible to properly adjust the coherence optical system 200 using the first front image, and the fundus illumination optical system 10 or the fundus photography optical system 30 using the second front image.

<Position Alignment Operation Using Front Image>

A photographic operation of the device with the above-mentioned configuration will be described. When a photography start switch is operated, the control unit 70 starts to capture an image. Naturally, the device may be configured such that photography is started automatically after the setting of photographic conditions is completed. In the photographic operation, the control unit 70 acquires the first front image via a third photography optical system when a first image is acquired via a first photography optical system. In addition, the control unit 70 acquires the second front image different from the first front image via the third photography optical system when a second image is acquired via a second photography optical system.

For example, the first image is an image of the subject's eye captured by performing a first type of photography. The second image is an image of the subject's eye captured by performing a second type of photography different from the first type of photography. The front images (the first front image and the second front image) are front images of the subject's eye by performing a third type of photography different from the first type method and the second type of photography.

For example, each of the first type of photography and the second type of photography may be configured to use the coherence optical system 200, an SLO optical system, the fundus camera optical system 100, the anterior chamber observation optical system 60, a perimeter, and the like.

For example, the SLO optical system includes a light scanner that scans measurement light (for example, the infrared light) emitted from a light source in two dimensions, and a photodetector that receives fundus-reflected light via a confocal opening disposed substantially conjugately with the fundus, and the SLO optical system has the same configuration as that of a so-called scanning laser ophthalmoscope (SLO). When a front image of the fundus is acquired, a front image (an SLO image) of the fundus based on a photodetection signal output from the photodetector of the SLO.

The fundus camera optical system 100 illuminates the fundus of the subject's eye by illumination light, and captures a front image of the fundus illuminated by the illumination light. When a method of capturing the second image is adopted in the fundus camera optical system 100, the visible light is used as the illumination light, and a color fundus image is captured as the second image. At this time, the second photography optical system has a visible light illumination optical system that illuminates the fundus of the subject's eye by the visible light, and a visible light photography optical system that captures a front image of the fundus of the subject's eye illuminated by the visible light, and the second photography optical system captures a color fundus image of the subject's eye as the second image. The color fundus image may be a fluorescent image acquired using fundus illumination light having a predetermined specified wavelength.

For example, the third type of photography may be configured to use the fundus camera optical system 100, the SLO optical system, and the like. When a method of capturing a front image is adopted in the fundus camera optical system 100, the infrared light is used as the illumination light, and an infrared fundus image is captured as the front image. At this time, the third photography optical system has an infrared light illumination optical system that illuminates the fundus of the subject's eye by the infrared light, and an infrared light photography optical system that captures a front image of the fundus of the subject's eye illuminated by the infrared light, and the third photography optical system captures an infrared fundus image of the subject's eye as the front images (the first front image and the second front image which will be described later).

<Analysis Process>

When the images are acquired, the control unit 70 performs an image analysis process. The control unit 70 detects the amount of positional deviation between the first front image and the second front image, and correlates the first image with the second image based on the amount of positional deviation.

It is possible to easily and accurately correlate the first image with the second image by correlating the first image with the second image using the front images captured in the same photographic conditions. Since it is possible to rapidly acquire infrared fundus images used as front images (the first front image and the second front image), when the first image is acquired, it is possible to rapidly acquire the front images that are positionally aligned when the first image is acquired. In addition, when the second image is acquired, it is possible to rapidly acquire the front images that are positionally aligned when the second image is acquired. For this reason, there is no nearly positional deviation present between the front images and other images (the first image and the second image). That is, in other words, since it is not necessary to correlate the positions of the front images with those of the other images, the amount of positional deviation between the first front image and the second front image can be applied as the amount of positional deviation between the first image and the second image. For this reason, it is possible to easily and accurately correlate the first image with the second image without performing a correlation between the images multiple times.

Hereinafter, an example of a process in which the control unit 70 detects the amount of positional deviation between the first front image and the second front image and correlates the first image with the second image based on the amount of positional deviation will be described. For example, a tomographic image is used as the first image. A color fundus image is used as the second image. An infrared fundus image is used as the front image. At this time, the control unit 70 specifies an acquisition position of a tomographic image of the fundus of the subject's eye captured by the first photography optical system on a color fundus image of the subject's eye captured by the second photography optical system by correlating the tomographic image of the fundus of the subject's eye with the color fundus image of the subject's eye. The control unit 70 superimposes a display on the color fundus image of the subject's eye based on the specified acquisition position, the display being indicative of the acquisition position in which the tomographic image of the fundus of the subject's eye is acquired. Since the inspector can accurately understand a correlation between the color fundus image and the tomographic image which have good resolution and good contrast, and are suitable to find lesions from the entirety of the fundus, the inspector can perform a useful diagnosis of the subject.

When images are acquired as described in the above-mentioned example, the control unit 70 acquires the first front image via the third photography optical system. After the control unit 70 acquires the first front image, the control unit 70 acquires the first image via the first photography optical system. After the control unit 70 acquires the first image, the control unit 70 acquires the second image via the third photography optical system. After the control unit 70 acquires the second front image, the control unit 70 acquires the second image via the second photography optical system. It is possible to easily capture the fundus of the subject's eye by acquiring a series of images in the above-mentioned sequence of image acquisition. That is, when the color fundus image is first captured, the pupil of the subject's eye is contracted, and thereby measurement light for tomographic image photography is unlikely to be incident on the subject's eye, and it is difficult to acquire a tomographic image 83; however, it is possible to easily acquire a tomographic image 83 and the color fundus image by acquiring a series of images in the above-mentioned sequence of image acquisition. Also, in a case where front images for correlation are acquired when the tomographic image 83 and the color fundus image are acquired, even though it takes a certain amount of time to acquire the tomographic image, it is possible to easily and accurately correlate the tomographic image with the color fundus image using a first infrared fundus image acquired when the tomgoraphic image is acquired and a second infrared fundus image acquired when the color fundus image is acquired.

In addition, in a case where front images for correlation are acquired when the tomgraphic image and the color fundus image are acquired, and the tomographic image photography is performed multiple times, it is possible to easily and accurately correlate a plurality of tomographic images with the color fundus image without capturing a plurality of color fundus images. For example, the control unit 70 acquires infrared fundus images when a plurality of tomographic images are acquired. The control unit 70 calculates the amount of positional deviation between each of the infrared fundus images acquired when the plurality of tomographic images are acquired, and the second infrared fundus image when the color fundus image is acquired. The control unit 70 correlates the plurality of tomographic images with one color fundus image based on the amount of positional deviation between each of the infrared fundus images and the second infrared fundus image. Accordingly, it is not necessary to acquire the color fundus image whenever acquiring the tomographic image, and when capturing the color fundus image, it is possible to less frequently illuminate the subject's eye by the visible light, and to reduce a burden on the subject. The plurality of tomographic images may be captured according to the same scanning pattern, or different scanning patterns (for example, a line scan, a cross scan, and a map scan).

The application of the technology of the present invention is not limited to the device disclosed in this embodiment. For example, an ophthalmic photography software (program) to perform the functions of the embodiment is supplied to a system or a device via a network or various storage media. A computer (for example, a CPU) of the system or the device can read the program, and execute the program.

For example, the ophthalmic photography program is executed by a processor of a control device that controls the operation of an ophthalmic photography device configured to capture the subject's eye. The ophthalmic photography program may be configured to include a first image acquisition step of acquiring the first image of the subject's eye by capturing the subject's eye by performing the first of photography; a second image acquisition step of acquiring the second image of the subject's eye by capturing the subject's eye by performing the second type of photography different from the first type of photography; a third image acquisition step of acquiring a front image of the subject's eye by capturing the subject's eye by performing the third type of photography different from the first type and the second type of photography, acquiring the first front image when the first image is acquired, and acquiring the second front image different from the first front image when the second front image is acquired; and an image processing step of detecting the amount of positional deviation between the first front image and the second front image, and correlating the first image with the second image based on the amount of positional deviation.

EXAMPLE

As illustrated in FIG. 1(a), a device main body 1 in this example mainly includes a base 4; a photography unit 3; a face support unit 5; and an operation unit 74. The photography unit 3 may accommodate an optical system (to be described later). The photography unit 3 may be provided so as to able to move with respect to the subject's eye E in three-dimensional directions (X, Y, and Z directions). The face support unit 5 may be fixed to the base 4 so as to support a subject's face.

An XYZ drive unit 6 may move the photography unit 3 relative to the eye E in a lateral direction, a vertical direction (the Y direction), and a forward and backward direction. The photography unit 3 may move with respect to the right and left eyes in the lateral direction (the X direction) and the forward and backward (operation distance) direction (the Z direction) due to the movement of a moving base 2 with respect to the base 4.

A joystick 74a is an operation member operated by an inspector so as to move the photography unit 3 with respect to the eye E. Naturally, the operation member is not limited to the joystick 74a, and another operation member (for example, a touch panel or a trackball) may be adopted.

For example, the operation unit transmits an operation signal from the inspector to the control unit 70. At this time, the control unit 70 may send the operation signal to a personal computer 90 (to be described later). In addition, the personal computer 90 sends a control signal to the control unit 70 in response to the operation signal. When the control unit 70 receives the control signal, the control unit 70 performs various control operations based on the control signal.

The moving base 2 moves with respect to the subject's eye by the operation of the joystick 74a. When a rotating knob 74b is rotated, the XYZ drive unit 6 is Y driven, and the photography unit 3 moves in the Y direction. In a case where the moving base 2 is not provided, the XYZ drive unit 6 may be configured to move the photography unit 3 with respect to the subject's eye when the joystick 74a is operated.

The photography unit 3 may be provided with the display unit 75 (for example, the display unit 75 is disposed so as to face the inspector). The display unit 75 may display a fundus observation image, a fundus photographic image, an anterior chamber observation image, or the like.

The device main body 1 in this example is connected to the personal computer (hereinafter, a PC) 90. For example, the display unit 95 and operation members (for example, a keyboard 96 and a mouse 97) may be connected to the PC 90.

Figure 2:
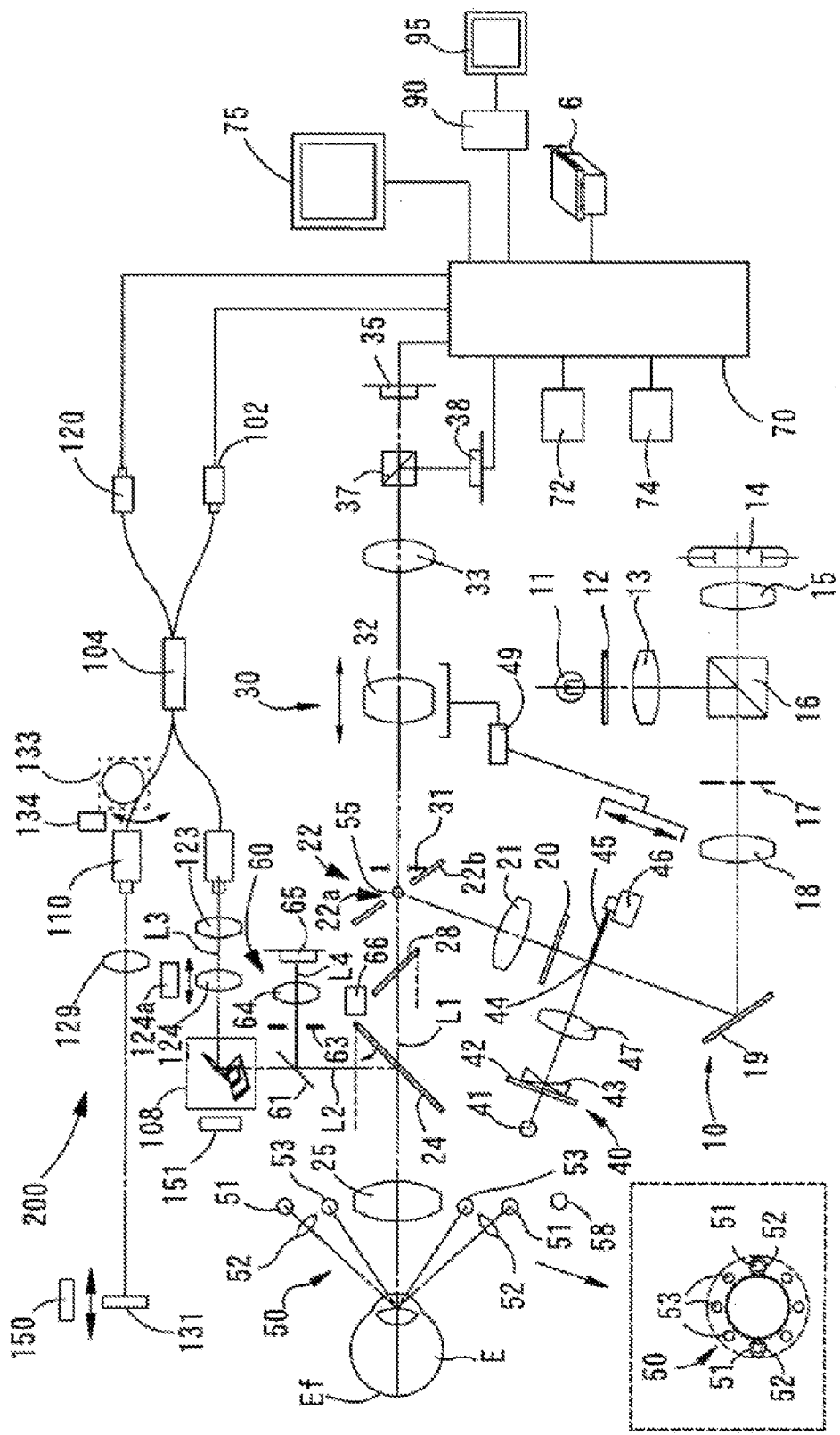
FIG. 2 is a view illustrating an optical system and a control system of the fundus photography device according to the embodiment.

As illustrated in FIG. 2, the optical system in this example mainly includes the illumination optical system 10; the photography optical system 30; and the coherence optical system (hereinafter, also referred to as an OCT optical system) 200. The optical system may further include the focus index projection optical system 40; the alignment index projection optical system 50; and the anterior chamber observation optical system 60. The illumination optical system 10 and the photography optical system 30 are used as a fundus camera optical system (an FC optical system) 100 that obtains a color fundus image by capturing the fundus using visible light (for example, a non-mydriatic state). The photography optical system 30 captures an image of the fundus of the subject's eye. The OCT optical system 200 obtains non-invasively a tomographic image of the fundus of the subject's eye by using optical coherence tomography.

<Fundus Camera Optical System (FC Optical System)>

Hereinafter, an example of an optical disposition of the fundus camera optical system 100 will be described.

<Illumination Optical System>

For example, the illumination optical system 10 has an observation illumination optical system and a photography illumination optical system. The photography illumination optical system mainly includes the photography light source 14; a condensing lens 15; a ring slit 17; a relay lens 18; a mirror 19; a black point plate 20; a relay lens 21; the hole mirror 22, and the objective lens 25. A flashlamp, an LED, or the like may be used as the photography light source 14. The black point plate 20 has a black point in a center portion thereof. The photography light source 14 is used so as to capture the fundus of the subject's eye using light in a visible bandwidth.

The observation illumination optical system mainly includes the observation light source 11, an infrared filter 12, a condensing lens 13, a dichroic mirror 16, and the optical system from the ring slit 17 to the objective lens 25. A halogen lamp, an LED, or the like may be used as the observation light source 11. For example, the observation light source 11 is used so as to observe the fundus of the subject's eye using light in a near-infrared bandwidth. The infrared filter 12 is provided so as to allow near-infrared light having a wavelength of 750 nm or greater to transmit therethrough, and to cut off light having a wavelength less than 750 nm. The dichroic mirror 16 is disposed between the condensing lens 13 and the ring slit 17. The dichroic mirror 16 has characteristics of reflecting light from the observation light source 11, and allowing light from the photography light source 14 to transmit therethrough. The observation light source 11 and the photography light source 14 may be disposed in series on the same optical axis.

<Photography Optical System>

For example, the objective lens 25, a photographic diaphragm 31, the focusing lens 32, an imaging lens 33, and the imaging element 35 are mainly disposed in the photography optical system 30. The photographic diaphragm 31 is positioned in the vicinity of an opening of the hole mirror 22. The focusing lens 32 can move in the optical axis direction. The imaging element 35 can be used for sensitive photography in a visible bandwidth. The photographic diaphragm 31 is disposed substantially conjugately with the pupil of the subject's eye E with respect to the objective lens 25. The focusing lens 32 is moved in the optical axis direction by the driving of a moving mechanism 49 equipped with a motor.

The dichroic mirror 37 is disposed between the imaging lens 33 and the imaging element 35, and has characteristics of reflecting infrared light and a part of visible light and allowing a majority of visible light to transmit therethrough. The observation imaging element 38 having sensitivity in an infrared bandwidth is disposed in a reflection direction of the dichroic mirror 37. A flip-up mirror may be used in place of the dichroic mirror 34. For example, the flip-up mirror is inserted on the optical path when the fundus is observed, and is retracted when an image of the fundus is captured.

The insertable and removable dichroic mirror (a wavelength selective mirror) 24 as an optical path division member is diagonally provided between the objective lens 25 and the hole mirror 22. The dichroic mirror 24 reflects the wavelength light of OCT measurement light and the wavelength light (for example, light having a center wavelength λ of 940 nm) from the alignment index projection optical system 50 and the anterior chamber illumination light source 58. The dichroic mirror 24 has characteristics of allowing light having a wavelength of 800 nm or less to transmit therethrough, the light containing the wavelength (for example, the center wavelength of 780 nm) of the fundus observation illumination light source. The dichroic mirror 24 is flipped up during the photography in conjunction with the driving of an insertion and removal mechanism 66, and is retracted out of the optical path. The insertion and removal mechanism 66 can be configured to include a solenoid, a cam, and the like.

Optical path corrective glass 28 is disposed closer to the imaging element 35 than the dichroic mirror 24, and can be flipped up by the driving of the insertion and removal mechanism 66. The optical path corrective glass 28 serves to correct the position of the optical axis L1 shifted by the dichroic mirror 24, when being inserted on the optical path.

Luminous flux emitted from the observation light source 11 is transformed into infrared luminous flux by the infrared filter 12, and the infrared luminous flux is reflected by the condensing lens 13 and the dichroic mirror 16, and illuminates the ring slit 17. The light that transmits through the ring slit 17 reaches the hole mirror 22 via the relay lens 18, the mirror 19, the black point plate 20, and the relay lens 21. The light reflected by the hole mirror 22 transmits through the corrective glass 28 and the dichroic mirror 24, and after the light is converged in the vicinity of the pupil of the subject's eye E by the objective lens 25, the light disperses and illuminates the anterior chamber of the subject's eye.

The reflected light from the fundus is imaged on the imaging element 38 via the objective lens 25, the dichroic mirror 24, the corrective glass 28, the opening of the hole mirror 22, the photographic diaphragm 31, the focusing lens 32, the imaging lens 33, and the dichroic mirror 37. The imaging element 38 is disposed conjugately with the fundus. An output from the imaging element 38 is input to the control unit 70, and the control unit 70 displays a fundus observation image (an OCT front image 82) of the subject's eye captured by the imaging element 38 on the display unit 75 (refer to FIG. 3).

Luminous flux emitted from the photography light source 14 transmits through the dichroic mirror 16 via the condensing lens 15. Thereafter, the fundus is illuminated by visible light via the same optical path as that of the illumination light for the observation of the fundus. The reflected light from the fundus is imaged on the imaging element 35 via the objective lens 25, the opening of the hole mirror 22, the photographic diaphragm 31, the focusing lens 32, and the imaging lens 33.

<Focus Index Projection Optical System>

The focus index projection optical system 40 mainly includes an infrared light source 41; a slit index plate 42; two declination prisms 43; a projection lens 47; and a spot mirror 44 diagonally provided on the optical path of the illumination optical system 10. The two declination prisms 43 are attached to the slit index plate 42. The spot mirror 44 is diagonally provided on the optical path of the illumination optical system 10. The spot mirror 44 is fixedly attached to the tip of a lever 45. Typically, the spot mirror 44 is provided diagonally with respect to the optical axis, and is retracted out of the optical path at a predetermined time before the photography by the rotation of the shaft of a rotary solenoid 46.

The spot mirror 44 is disposed conjugately with the fundus of the subject's eye E. The light source 41, the slit index plate 42, the declination prisms 43, the projection lens 47, the spot mirror 44, and the lever 45 are moved in the optical axis direction in conjunction with the focusing lens 32 by the driving of the moving mechanism 49. After luminous flux from the slit index plate 42 of the focus index projection optical system 40 is reflected by the spot mirror 44 via the declination prisms 43 and the projection lens 47, the luminous flux is projected on the fundus of the subject's eye E via the relay lens 21, the hole mirror 22, the dichroic mirror 24, and the objective lens 25. When the fundus is not in focus, index images S1 and S2 are projected on the fundus while being separated from each other in response to a deviation direction and the amount of deviation. In contrast, when the fundus is in focus, the index images S1 and S2 are projected on the fundus while matching each other (refer to FIG. 3). The index images S1 and S2 are captured along with a fundus image by the imaging element 38.

<Alignment Index Projection Optical System>

As illustrated in a dotted line box on the left in FIG. 2, the alignment index projection optical system 50 configured to project alignment index luminous flux has a plurality of infrared light sources disposed at 45 degree intervals concentrically about the photography optical axis L1. An ophthalmic photography device in this example mainly includes a first index projection optical system (at 0 degrees and 180 degrees) and a second index projection optical system. The first index projection optical system has an infrared light source 51 and a collimating lens 52. The second index projection optical system is disposed at a position different from that of the first index projection optical system, and has six infrared light sources 53. The infrared light sources 51 are disposed to be bilaterally symmetrical while a perpendicular plane passing through the photography optical axis L1 is interposed between the infrared light sources 51. In this case, the first index projection optical system laterally projects infinite indexes on a cornea of the subject's eye E. The second index projection optical system is configured to vertically or diagonally project finite indexes on the cornea of the subject's eye E. FIG. 2 illustrates the first index projection optical system (at 0 degrees and 180 degrees) and only a part of the second index projection optical system (at 45 degrees and 135 degrees) for illustrative purposes.

<Anterior Chamber Observation Optical System>

The anterior chamber observation (photography) optical system 60 configured to capture the anterior chamber of the subject's eye mainly includes the dichroic mirror 61, a diaphragm 63, the relay lens 64, and the two-dimensional imaging element 65 (a photodetector: hereinafter, may be briefly referred to as the imaging element 65) on a reflection side of the dichroic mirror 24. The imaging element 65 has sensitivity in an infrared bandwidth. The imaging element 65 also acts as imaging means for the detection of an alignment index, and captures an image of the anterior chamber illuminated by infrared light emitted from the anterior chamber illumination light source 58 and an image of the alignment index. The anterior chamber illuminated by the anterior chamber illumination light source 58 is received by the imaging element 65 via the objective lens 25, the dichroic mirror 24, and the optical system from the dichroic mirror 61 to the relay lens 64. Alignment luminous flux emitted from the light source of the alignment index projection optical system 50 is projected on the cornea of the subject's eye. The cornea-reflected image is received (projected on) by the imaging element 65 via the objective lens 25 to the relay lens 64.

Figure 4A:
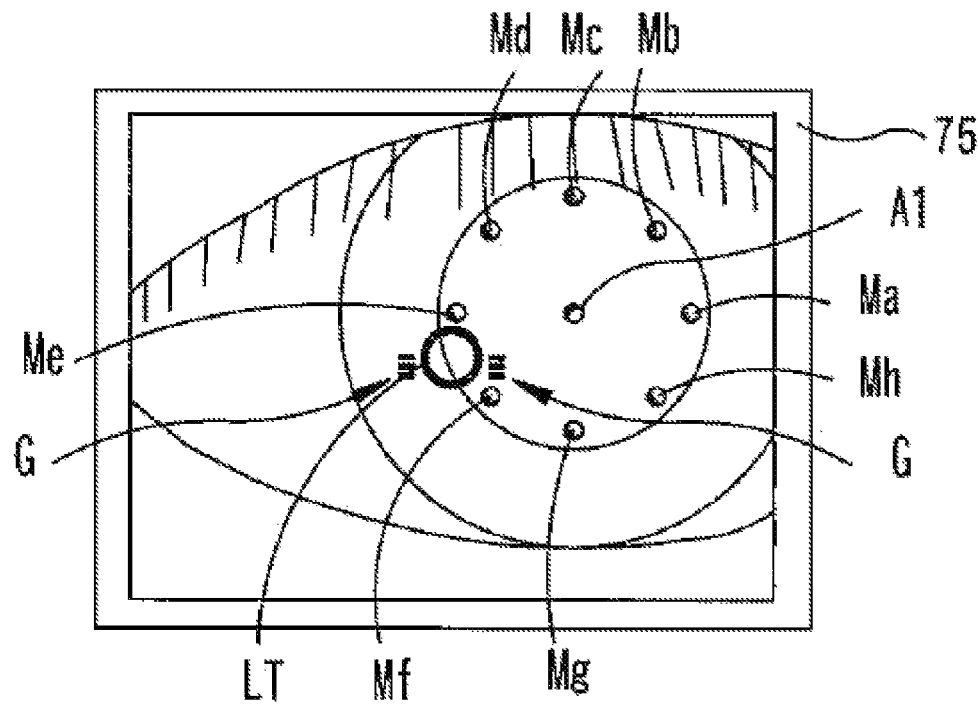
FIGS. 4A and 4B illustrate an example in which an anterior chamber image captured by an imaging element is displayed on the display unit.
Figure 4B:
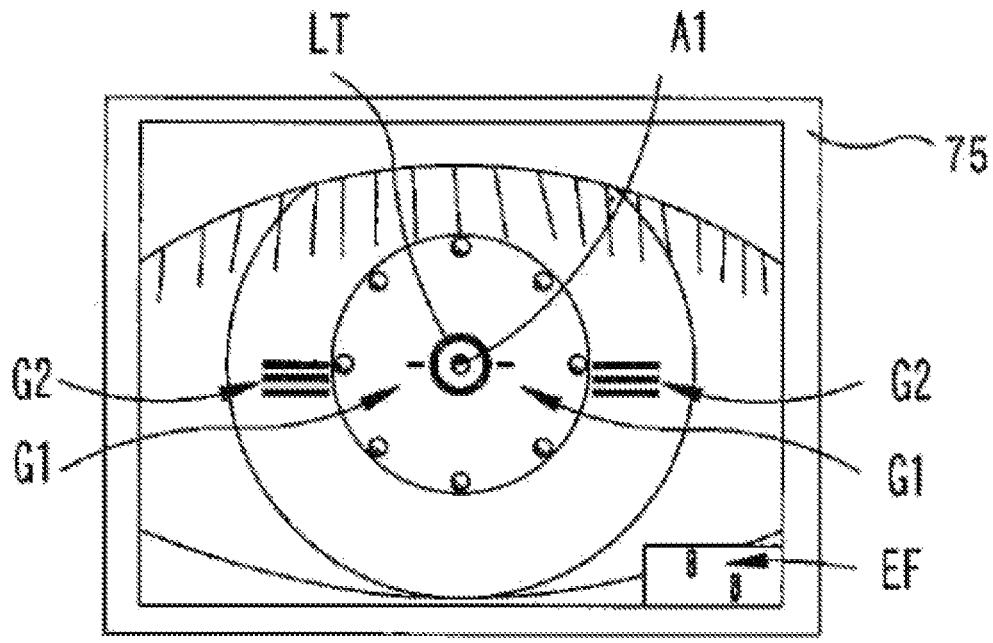

An output from the two-dimensional imaging element 65 is input to the control unit 70, and as illustrated in FIGS. 3 and 4, the display unit 75 displays an anterior chamber image captured by the two-dimensional imaging element 65. The anterior chamber observation optical system 60 is also used as a detection optical system that detects a state of alignment of the device main body with respect to the subject's eye.

The infrared light sources 55 (in the embodiment, two infrared light sources 55 are disposed; however, the number of infrared light sources 55 is not limited to two) are disposed in the vicinity of a hole of the hole mirror 22, and are used so as to form an optical alignment index (a working dot W1) on the cornea of the subject's eye. The light source 55 may be configured to guide infrared light to an optical fiber, an end surface of which is disposed in the vicinity of the hole mirror 22. When an operation distance between the subject's eye E and the photography unit (the device main body) 3 is appropriate, the cornea-reflected light produced by the light source 55 is imaged on an imaging surface of the imaging element 38. Accordingly, the inspector performs a fine adjustment of alignment using the working dot formed by the light source 55 in a state where the fundus image is displayed on a monitor 8.

<OCT Optical System>

The following description is given with reference to FIG. 2. The OCT optical system 200 is configured like a so-called optical coherence tomography (OCT)-based ophthalmic device, and captures a tomographic image of the eye E. In the OCT optical system 200, a coupler (an optical divider) 104 divides light emitted from the measurement light source 102 into measurement light (sample light) and reference light. The OCT optical system 200 guides the measurement light to the fundus Ef of the eye E, and guides the reference light to a reference optical system 110. The measurement light reaches the scanning unit 108 via a collimator lens 123 and a focus lens 124, and a reflected direction of the measurement light is changed by the driving of two galvanometer mirrors. After the measurement light reflected by the scanning unit 108 is reflected by the dichroic mirror 24, the measurement light concentrates on the fundus of the subject's eye via the objective lens 25. Coherence light obtained by combining the measurement light reflected by the fundus Ef and the reference light is received by the detector (photodetector) 120.

The detector 120 detects a state of coherence between the measurement light and the reference light. When Fourier domain OCT is adopted, the spectral intensity of the coherence light is detected by the detector 120, and a predetermined range of a depth profile (A scan signal) is acquired by Fourier-converting spectral intensity data. For example, spectral-domain OCT (SD-OCT) or swept-source OCT (SS-OCT) may be adopted. When the spectral-domain OCT (SD-OCT) is adopted, a wide bandwidth light source is used as the light source 102, and a spectrometer is used as the detector 120. When the swept-source OCT is adopted, a variable wavelength light source is used as the light source 102, and a single photodiode is used as the detector 120 (the detection of equilibrium may be performed). In addition, time-domain OCT (TD-OCT) may be adopted.

The scanning unit 108 scans light emitted from the measurement light source on the fundus of the subject's eye. For example, the scanning unit 108 scans the measurement light on the fundus in two dimensions (in an X-Y direction (vertical direction)). The scanning unit 108 is disposed substantially conjugately with the pupil. For example, the scanning unit 108 is two galvanometer mirrors, and a reflected angle of the scanning unit 108 is arbitrarily adjusted by a drive unit 151.

Accordingly, a reflected (advance) direction of luminous flux emitted from the light source 102 is changed, and is scanned on the fundus in an arbitrary direction. Accordingly, an imaging position on the fundus Ef is changed. The scanning unit 108 may be configured to deflect light. For example, an acousto optical modulator (AOM) other than a reflective mirror (a galvanometer mirror, a polygon mirror, or a resonant scanner) may be used so as to change an advance (deflection) direction of light.

The reference optical system 110 generates the reference light to be combined with the reflected light acquired by the reflection of the measurement light from the fundus Ef. The reference optical system 110 may be Michelson type or may be Mach-Zehnder type.

The reference optical system 110 may change an optical path length difference between the measurement light and the reference light by moving an optical member on the reference optical path. For example, a reference mirror 131 moves in an optical axis direction. The configuration of changing the optical path length difference may be disposed on the measurement optical path of the measurement optical system.

More specifically, the reference optical system 110 mainly includes a collimator lens 129, the reference mirror 131, and a reference mirror drive unit 150. The reference mirror drive unit 150 is disposed on the reference optical path, and is configured such that the reference mirror drive unit 150 can move in the optical axis direction so as to change the optical path length of the reference light. The light is reflected by the reference mirror 131, and thereby the light returns to the coupler 104 again, and is guided to the detector 120. In another example, the reference optical system 110 may be a transmittance optical system (for example, an optical fiber), and light from the coupler 104 does not return, transmits through the transmittance optical system, and is guided to the detector 120.

<Control Unit>

Figure 6A:
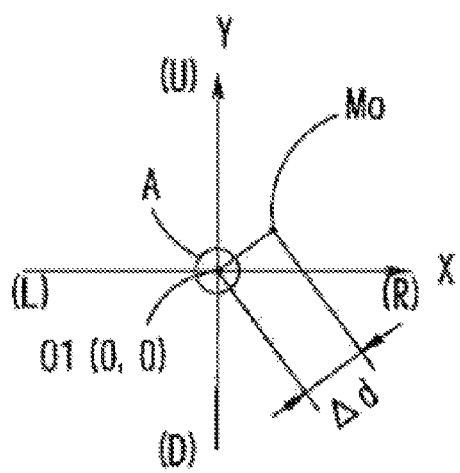
FIGS. 6A and 6B show graphs illustrating the detection of alignment with respect to a subject's eye.
Figure 6B:
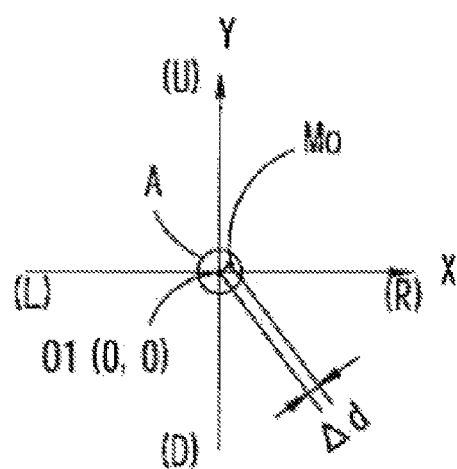

Subsequently, a control system in this example will be described with reference to FIG. 6. As illustrated in FIG. 6, the following are connected to the control unit 70 in this example: the imaging element 65 for anterior chamber observation; the imaging element 38 for infrared fundus observation; the display unit 75; the operation unit 74; a HUB 71 compliant with USB 2.0 standards; various light sources (not illustrated); various actuators (not illustrated); and the like. The USB 2.0 compliant HUB 71 is connected to the imaging element 35 built into the device main body 1 and the personal computer (PC) 90.

The PC 90 includes a CPU 91 as a processor; an operation input unit (for example, a mouse, a keyboard); a memory (a non-volatile memory) 72 as storage means; and a display unit 95. The CPU 91 may control the device main body 1. The memory 72 is a non-transitory storage medium that can maintain stored content even when the supply of electrical power is shut off. For example, the memory 72 may be a USB memory insertably and removably mounted on a hard disc drive, a flash ROM, or the PC 90, an external server, or the like. The memory 72 stores a photography control program for controlling the device main body (ophthalmic photography device) 1 to capture a front image and a tomographic image.

The memory 72 stores an ophthalmic analysis program that is used when the PC 90 is used as an ophthalmic analysis device. That is, the PC 90 may also be used as the ophthalmic analysis device. The memory 72 stores various pieces of information regarding photography, for example, information regarding a tomographic image (OCT data) in scanning lines, a three-dimensional tomographic image (three-dimensional OCT data), a fundus front image, and a photographic position of a tomographic image. The operation input unit receives various operation instructions from the inspector.

The detector (for example, a line CCD) 120 for OCT photography built into the device main body 1 is connected to the PC 90 through a USB signal line via USB ports 79*a* and 79*b*. In this example, as such, the device main body 1 and the PC 90 are connected to each other through two USB signal lines 76 and 77.

The control unit 70 may detect an alignment index from an anterior chamber observation image 81 captured by the imaging element 65, and process the alignment index. The control unit 70 may detect the amount of deviation of the alignment of the device main body 1 with respect to the subject's eye based on an imaging signal from the imaging element 65.

The control unit 70 may electronically form and display a reticle (an alignment reference) LT at a predetermined position on a screen of the display unit 75 as illustrated on an anterior chamber image observation screen in FIG. 4. The control unit 70 may control a display of an alignment index A1 in such a manner that a relative distance between the alignment index A1 and the reticle LT is changed based on the detected amount of alignment deviation.

The control unit 70 displays the anterior chamber observation image captured by the imaging element 65, and the anterior chamber observation image captured by the imaging element 38 on the display unit 75 of the main body.

The control unit 70 streamingly outputs the anterior chamber observation image and the fundus observation image to the PC 90 via the HUB 71 and the USB 2.0 ports 78*a* and 78*b*. The PC 90 displays the anterior chamber observation image and the fundus observation image 82 (which are streamingly output) on the display unit 95 of the PC 90. The anterior chamber observation image and the fundus observation image (the anterior chamber observation image 81 and the FC front image 82 in FIG. 3) may be simultaneously displayed as live images (for example, live front images) on the display unit 95.

The imaging element 35 captures a color fundus image based on a trigger signal from the control unit 70. The color fundus image is also output to the control unit 70 and the PC 90 via the HUB 71 and the USB 2.0 ports 78*a* and 78*b*, and is displayed on the display unit 75 or the display unit 95 of the PC 90.

In addition, the detector 120 is connected to the PC 90 via the USB ports 79*a* and 79*b*. A photodetection signal from the detector 120 is input to the PC 90. The PC 90 (more specifically, the processor (for example, CPU) of the PC 90) generates the tomographic image 83 by computationally processing the photodetection signal from the detector 120.

For example, when the Fourier domain OCT is adopted, the PC 90 processes a spectroscopic signal containing a coherence signal of each wavelength output from the detector 120. The PC 90 obtains inside information (for example, depth data of the subject's eye (depth information)) regarding the subject's eye by processing the spectroscopic signal. More specifically, the spectroscopic signal (spectral data) is written as a function of the wavelength $\lambda$, and is converted into an equal interval function I (k) of a wavenumber k ($=2\pi/\lambda$). The PC 90 obtains a signal distribution in a depth (in the Z direction) region by Fourier-converting the spectroscopic signal in a space of the wavenumber k.

In addition, the PC 90 may obtain information (for example, a tomographic image) regarding the subject's eye along with inside information obtained at different positions by the scanning of measurement light. The PC 90 stores an obtained result in the memory 72. The PC 90 may display the obtained result on the display unit 95.

The device main body 1 performs photography according to a pre-set scanning pattern based on a release signal from the PC 90. The PC 90 processes photographic signals, and outputs an imaging result on the display unit 95 of the PC 90.

At this time, the detector 120 outputs detection signals to the PC 90. The PC 90 generates a tomographic image from the detection signals from the detector 120.

The PC 90 transmits the generated tomographic image to the device main body 1 via the USB 2.0 ports 78*a* and 78*b* and the HUB 71. The control unit 70 displays the transmitted tomographic image 83 on the display unit 75 (for example, refer to the tomographic image 83). The PC 90 may generate an OCT front image from the output signals from the detector 120, and display the OCT front image 84 on the display unit 75 or the display unit 95.

Figure 1B:
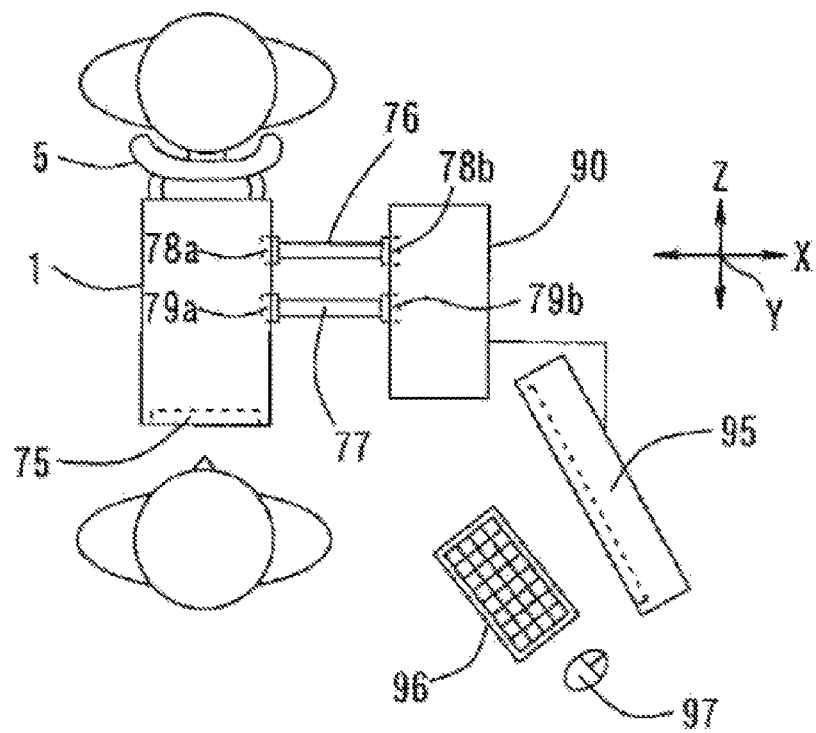

In this example, the inspector can perform set operations such as a setting for OCT photography, alignment, or optimization, or perform a positional alignment, while watching the display unit 75 provided in the device main body 1 (details will be described later). Accordingly, as illustrated in FIG. 1(*b*), the inspector is not required to put effort into alternately confirming the display unit 75 of the device main body 1 and the display unit 95 of the PC 90 which are disposed at different positions. In addition, when the inspector opens an eyelid and performs photography, it may be easier for the inspector to open the eyelid while confirming the display unit 75 than opening the eyelid while confirming the display unit 95 of the PC 90.

In addition, since the tomographic image 83, the OCT front image 84, the FC front image 82, the anterior chamber observation image 81, and the like are displayed on both the display unit 75 and the display unit 95 of the PC 90, the inspector can preferably select between an operation via the device main body 1 and an operation via the PC 90. Since various captured images are displayed on both the display unit 75 and the display unit 95 of the PC 90, it is possible to increase the number of screens on which images can be observed, and two or more persons can easily confirm the images.

When one inspector observes images on the display unit 95 of the PC 90, and the other inspector performs photography using the device main body 1, that is, two inspectors separately perform a measurement, the inspector who performs photography can confirm the captured tomographic image 83 on the display unit 75, and can redo the photography when the photography cannot be well performed. For this reason, it is less frequent for the inspector who observes the display unit 95 to notify the inspector who performs photography that the redoing of a measurement is required.

In this manner, since the tomgoraphic image 83 is displayed on both the display unit 75 of the device main body 1 and the display unit 95 of the PC 90, the device main body 1 is adaptable to a preferred type of photography of the inspector.

Similarly, this also applies to the color fundus photography. It may be possible to not only input a color fundus photography result to the PC 90, but also to transmit image information such as a preview result to the device main body 1 via the USB 2.0 ports 78*a* and 78*b* and the HUB 71, and to display a color fundus image on the display unit 75 of the device main body 1. Accordingly, the inspector is not required to put effort in alternately confirming the device main body 1 and the PC 90 so as to watch the color fundus image. In a case where the inspector operates the device main body 1 while watching the color fundus photography image, since the inspector is required to confirm only the display unit 75 without glancing the display unit 95 of the PC 90, the inspector has less burden.

<Observation Screen that Displays OCT Front Image and FC Front Image>

An example of a control operation of the device having the above-mentioned configuration will be described hereinbelow. For example, the control unit 70 may combine the anterior chamber observation image captured by the imaging element 65, the fundus observation image (hereinafter, the FC front image) captured by the imaging element 38, the OCT tomographic image (hereinafter, the tomographic image) from the PC 90, and the OCT front image, and display the combined image on an observation screen on the display unit 75. As illustrated in FIG. 3, the observation screen may simultaneously display the anterior chamber observation image 81, the FC front image 82, and the tomographic image 83 in a live mode.

FIG. 3 is a view illustrating an example of an observation screen according to the embodiment. The control unit 70 divisively displays a first display region 300 and a second display region 400 on the display unit 75. Here, captures captured by the coherence optical system 200 are integrally displayed in the first display region, and captures captured by the fundus illumination optical system 100 are integrally displayed in the second display region. In the embodiment, the first display region 300 and the second display region 400 are formed laterally side by side; however, naturally, the disposition of the first display region 300 and the second display region 400 is not limited to that in the embodiment. For example, the first display region 300 and the second display region 400 may be disposed vertically side by side. In the example given in the following description, the observation screen is displayed on the display unit 75; however, the display unit 95 may be controlled to display the same observation screen by the PC 90.

The following displays are formed in the first display region 300: an OCT front display region 310 (hereinafter, referred to as a display region 310); a scanning position set display (hereinafter, referred to as a set display) 320; a photographic condition display (hereinafter, referred to as a condition display) 330; a tomographic image display region (hereinafter, referred to as a display region) 340; and an optical path difference adjustment display 350.

The OCT front image 84 and the scanning line SL are displayed in the display region 310. The OCT front image 84 (may be simply referred to as a front image 84) is preferably a live image. The control unit 70 updates the front image 84 displayed in the display region 310 whenever a new OCT front image is acquired. When the OCT front image is displayed in a live mode, the control unit 70 may consecutively display the front images 84 in real time, or may update the front image at constant time intervals (for example, every 0.5 seconds).

The scanning line SL is a display for electronically indicating a scanning position (measurement position) on the OCT front image 84. The control unit 70 displays the scanning line SL superimposed on the OCT front image 84. The display pattern of the scanning line SL corresponds to the scanning pattern of the scanning unit 108. For example, when a line scan is set, the scanning line is displayed in a line. When a cross scan is set, the scanning line SL is displayed in a cross shape. When a map scan (raster scan) is set, the scanning line is displayed in a rectangular shape. A positional relationship between the display position of the scanning line SL and the scanning position of the scanning unit 108 is pre-set.

The set display 320 is a display through which the inspector sets the scanning position of the OCT. The control unit 70 controls the scanning unit 108 to change a scanning position on the fundus Ef based on an operation signal input via the set display 320. The control unit 70 changes the display position of the scanning line SL in conjunction with a change in the scanning position of the scanning unit 108.

The set display 320 of the embodiment has arrows for changing the scanning position the vertical direction and the lateral direction, and arrows for changing the scanning position in a clockwise direction and a counter-clockwise direction. The control unit 70 may change the scanning position by directing operating (for example, a drag scan) the scanning line SL.

The condition display 330 is a display region for illustrating the photographic conditions of the coherence optical system 200. For example, a photography mode, a scanning width, a scanning angle, a scanning density, the frequency of an addition task, and photographic sensitivity are displayed in the condition display 330. The combination of a captured portion and a scanning pattern can be selected as the photography mode, and the selected photography mode is displayed. In the photography mode illustrated in FIG. 3, a macular area is set as the captured portion, and a line scan is set as the scanning pattern. It is possible to change the photographic condition by operating a condition display displayed in the condition display 330. When a condition display corresponding to the scanning width is operated, the scanning width can be changed.

The OCT tomographic image (hereinafter, the tomographic image) 83 and an image evaluation display 345 are displayed in the display region 340.

The tomographic image 83 is preferably a live image. The control unit 70 updates the tomographic image 83 displayed in the display region 340 whenever a new tomographic image is acquired. When the tomographic image is displayed in a live mode, the control unit 70 may consecutively display the tomographic images 83 in real time, or may update the tomographic image at constant time intervals (for example, every 0.5 seconds).

Here, when the scanning line is changed as described above, the control unit 70 can display the tomographic image 83 corresponding to the changed scanning position. When a scanning pattern configured to include a plurality of scanning lines is set, the control unit 70 may display a tomographic image corresponding to each of the scanning lines.

The image evaluation display 345 is a display for evaluating whether the image quality of a tomographic image is good, and in the embodiment, evaluation is performed at ten levels using a bar graph. The PC 90 analyzes the acquired tomographic image, and evaluates the image based on an analysis result. The control unit 70 displays the analysis result transmitted from the PC 90 in the image evaluation display 345. When the analysis result is rated being low in the image evaluation display 345, the inspector may react to increase the photographic sensitivity, or to adjust the position of the photography unit 3 with respect to the patent's eye using the anterior chamber observation image 81.

The optical path difference adjustment display 350 is a display region through which an optical path length difference between the measurement light and the reference light is adjusted. When an automatic adjustment display (Auto Z)

is operated, the control unit 70 controls the drive unit 150 to automatically adjust the optical path length difference in such a manner that a tomographic image of the fundus is acquired.

When a manual adjustment display (arrows) is operated, the control unit 70 controls the drive unit 150 to adjust the optical path length difference in response to a direction of the operation and the amount of operation (operation time). Accordingly, the optical path length difference is finely adjusted by the manual operation performed by the inspector.

Subsequently, the second display region 400 will be described. The following displays are formed in the second display region 400: an FC front display region 410; an anterior chamber image display region 420; a photographic condition display (hereinafter, referred to as a condition display) 430; and a pupil diameter determination display 440.

The FC front image 82, focus index images S1 and S2, optical alignment index images (optical working dots) W1 and W2 are displayed in the display region 410. The FC front image 82 (may be simply referred to as a front image 82) is preferably a live image. The control unit 70 updates the FC front image 82 displayed in the display region 410 whenever a new FC front image is acquired. When the FC front image 82 is displayed in a live mode, the control unit 70 may consecutively display the FC front images 82 in real time, or may update the front image 82 at constant time intervals (for example, every 0.5 seconds).

When the alignment with respect to the subject's eye is properly performed to a certain level, the alignment indexes W1 and W2 appear on the front image 82 due to cornea-reflected light formed by the light source 55. The observation light is shielded by the lever 45 inserted on the optical path of the illumination optical system 10, and thereby a light shield region 415 is formed on the imaging element 38, and the optical focus index images S1 and S2 projected on the fundus are formed at the tip (on the optical axis) of the light shield region 415.

The anterior chamber observation image 81 is formed in the anterior chamber image display region 420. The anterior chamber observation image 81 is preferably a live image. The control unit 70 updates the anterior chamber observation image 81 displayed in the display region 420 whenever a new anterior chamber observation image is acquired. When the anterior chamber observation image is displayed in a live mode, the control unit 70 may consecutively display the anterior chamber observation images 81 in real time, or may update the anterior chamber observation image at constant time intervals (for example, every 0.5 seconds). In the embodiment, the anterior chamber image display region 420 is displayed smaller than the FC front display region 410. Naturally, a sizing relationship between the anterior chamber image display region 420 and the FC front display region 410 is not limited to that in the embodiment.

The condition display 430 is a display region in which the photographic conditions of the fundus camera optical system 100 are illustrated. For example, the following are displayed in the condition display 430: the amount of photography light emitted from the photography light source 14; the amount of diopter correction made by the focusing lens 32; a selection of a small-pupil photography mode; a short exposure photography mode; and the like. It is possible to change the photographic condition by operating an icon (or a condition display) displayed in the condition display 430. For example, when an icon corresponding to the amount of photography light is operated, the amount of photography light can be changed.

The pupil diameter determination display 440 displays whether the pupil diameter of the subject's eye satisfies a desired pupil diameter. In the processing of the anterior chamber observation image, it is determined whether a predetermined pupil diameter is satisfied, and based on a process result, it is determined whether the desired pupil diameter is satisfied. The control unit 70 changes a display state of the pupil diameter determination display 440 based on a determination result (details will be described later).

The presentation position of the fixation target may be adjusted in either one of the display region 340 and the display region 410. In this case, a mark indicative of the presentation position of the fixation target is displayed on any one of the front images, and the presentation position of the fixation target is changed by moving the mark on the display unit 75.

When the control unit 70 does not acquire the OCT front image 84, the control unit 70 may display an image in the display region 310, the image having a portion cut out corresponding to the FC front image 82.

<Sequence of Photography>

Hereinafter, an operation of the device will be described. The inspector gets the subject's face supported by the face support unit 5. The inspector instructs the subject to watch a fixation target (not illustrated). In an initial stage, the dichroic mirror 24 is inserted on the optical path of the photography optical system 30, and the display unit 75 displays the anterior chamber image captured by the imaging element 65.

The inspector moves the photography unit 3 in the vertical and lateral directions by adjusting alignment in the vertical and lateral directions, for example, by operating the joystick 74a, in such a manner that the anterior chamber image appears on the display unit 75. As illustrated in FIG. 4, when the alignment is adjusted in order for the anterior chamber image to appear on the display unit 75, eight index images (first alignment index images) Ma to Mh appear. At this time, the imaging range of the imaging element 65 preferably includes the pupil of the anterior chamber, an iris, and an eyelash when the alignment is completed.

<Alignment Detection and Automatic Alignment in X, Y, and Z Directions>

When the alignment index images Ma to Mh are detected by the two-dimensional imaging element 65, the control unit 70 starts automatic alignment control. The control unit 70 detects the amount Δd of deviation of the alignment of the photography unit 3 with respect to the subject's eye based on an imaging signal from the two-dimensional imaging element 65. More specifically, an X-Y coordinate of the center of a ring shape formed by the index images Ma to Mh projected in a ring shape is detected as a substantially center of the cornea, and the amount Δd of deviation between a pre-set alignment reference position O1 (for example, the intersection of an imaging surface of the imaging element 65 and the photography optical axis L1) on the imaging element 65 in the X and Y directions, and the center coordinate of the cornea is obtained (refer to FIG. 7). The center of the pupil may be detected by processing images, and an alignment deviation may be detected based on the amount of deviation between the coordinate position and the reference position O1.

The control unit 70 controls the driving of the XYZ drive unit 6 to perform automatic alignment in such a manner that the amount Δd of deviation is present in an alignment completion allowable range A. The suitability of the alignment in the X and Y directions is determined based on whether the amount Δd of deviation is continuously present in the alignment completion allowable range A for a constant amount of time (for example, for 10 frames of the image processing or 0.3 seconds) (whether an alignment condition A is satisfied).

In addition, the control unit 70 obtains the amount of alignment deviation in the Z direction by comparing the distance between the infinite index images Ma and Me and the distance between the finite index images Mh and Mf detected as described above. At this time, the control unit 70 obtains the amount of alignment deviation with the subject's eye in a direction of the operation distance based on characteristics by which when the photography unit 3 deviates in the direction of the operation distance, the distance between the infinite index images Ma and Me is not nearly changed, and the distance between the index images Mh and Mf is changed (specifically, refer to JP-A-6-46999).

The control unit 70 also obtains the amount of deviation in the Z direction with respect to an alignment reference position, and controls the driving of the XYZ drive unit 6 to perform automatic alignment in such a manner that the amount of deviation is present in an alignment completion allowable range. The suitability of the alignment in the Z direction is determined based on whether the amount of deviation in the Z direction is present in the alignment completion allowable range for a constant amount of time (whether an alignment condition is satisfied).

When the alignment in the X, Y, and Z directions satisfies the alignment completion condition via the alignment operation, the control unit 70 determines that the alignment in the X, Y, and Z directions is met, and proceeds to the next step.

Here, when the amount Δd of alignment deviation in the X, Y, and Z directions is present in an allowable range A1, the control unit 70 stops the driving of the drive unit 6, and outputs an alignment completion signal. Even after the alignment is completed, the control unit 70 frequently detects the amount Δd of deviation, and when the amount Δd of deviation exceeds the allowable range A1, the control unit 70 restarts automatic alignment. That is, the control unit 70 controls the photography unit 3 to track the subject's eye in such a manner that the amount Δd of deviation is present in the allowable range A1.

<Determination of Diameter of Pupil>

After the alignment is completed, the control unit 70 starts a process of determining whether the pupil of the subject's eye is in a suitable state. At this time, the suitability of a pupil diameter is determined based on whether a pupil edge from the anterior chamber image detected by the imaging element 65 is out of a predetermined pupil determination area. The pupil determination area is set to have the size of a diameter (for example, a diameter of 4 mm) around an image center (photography optical axis center), through which the fundus illumination luminous flux can pass. In a simple manner, four pupil edges detected laterally and vertically with respect to the image center are used. When the pupil edge points are out of the pupil determination area, the amount of illumination light for photography is sufficiently ensured (specifically, refer to JP-A-2005-160549 filed by the applicant). The suitability of the pupil diameter is continuously determined until the photography is performed, a determination result is displayed on the display unit 75.

<Detection of State of Focus and Autofocus>

Figure 5:
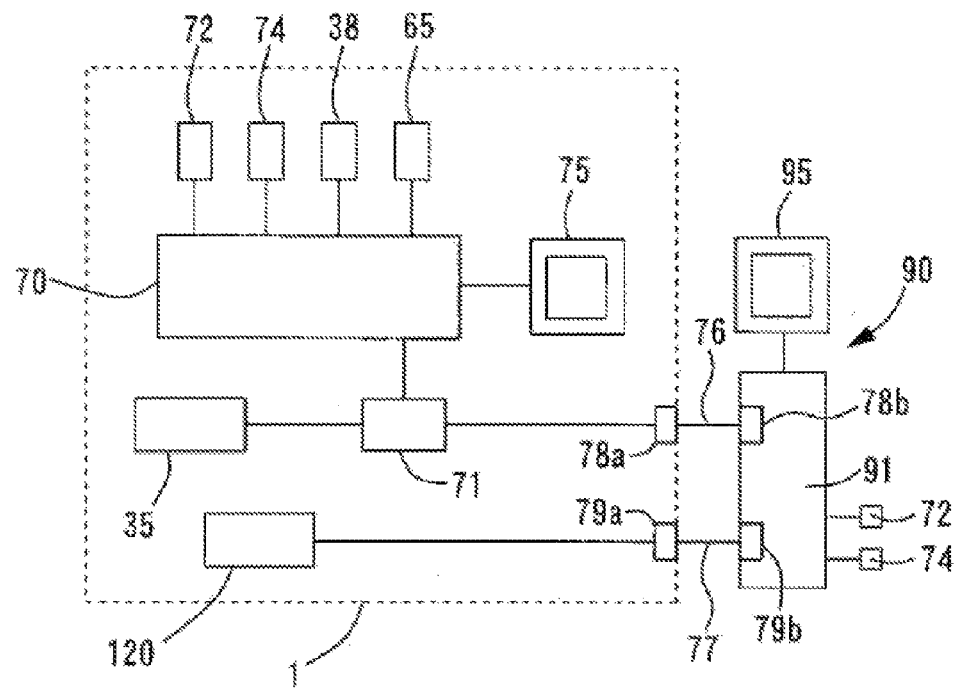
FIG. 5 is a block diagram illustrating the control system according to the embodiment.

When the alignment is completed using the imaging element 65, the control unit 70 performs an autofocus on the fundus of the subject's eye. FIG. 5 illustrates an example of a fundus image captured by the imaging element 38, and the focus index images S1 and S2 are projected to the center of the fundus image by the focus index projection optical system 40. Here, when the focus index images S1 and S2 are not in focus, the focus index images S1 and S2 are projected while being separated from each other, and when the focus index images S1 and S2 are in focus, the focus index images S1 and S2 are projected while matching each other. The control unit 70 detects the index images S1 and S2 by processing the images, and obtain information regrarding the separation of the images. The control unit 70 controls the driving of the moving mechanism 49 based on the information regarding the separation of the index images S1 and S2, and moves the lens 32 so as to focus on the fundus.

<Optimization Control>

When an alignment completion signal is output, the control unit 70 generates a trigger signal for starting optimization control, and starts an optimization control operation. When the control unit 70 performs the optimization control, the inspector can observe a desired fundus portion at high sensitivity and high resolution. In this embodiment, the optimization control is the controlling of an optical path length adjustment, a focus adjustment, and a polarization state adjustment (polarizer adjustment). In the optimization control, constant allowable conditions relative to the fundus can be preferably satisfied, and the best optimized state is not necessarily obtained via the optimization control.

In an initialization control of the optimization control, the control unit 70 sets the positions of the reference mirror 131 and the focusing lens 124 to initial positions, respectively. After the initialization control is completed, the control unit 70 performs a first optical path length adjustment (a first automatic optical path adjustment) by moving the reference mirror 131 from the set initial position by predetermined steps in one direction. In parallel with the first optical path length adjustment, the control unit 70 acquires focal position information (for example, the amount of movement of the lens 32) based on a result of a focus on the fundus of the subject's eye performed by the fundus camera optical system. When the focal position information is acquired, the control unit 70 performs an autofocus adjustment (focus adjustment) by moving the focusing lens 124 to a focal position. The focal position is preferably a position in which it is possible to acquire an allowable contrast of a tomographic image as an observation image, and the focal position is not necessarily an optimized focal position.

After the focus adjustment is completed, the control unit 70 performs a second optical path length adjustment in which an optical path length is re-adjusted (an optical path length is finely adjusted) by moving the reference mirror 131 in the optical axis direction again. After the second optical path length adjustment is completed, the control unit 70 adjusts a polarization state of measurement light by driving a polarizer 133 for adjusting a polarization state of reference light (specifically, refer to JP-A-2012-56292).

As such, when the optimization control is completed, the inspector can observe a desired fundus portion at high sensitivity and high resolution. The control unit 70 controls the driving of the scanning unit 108 to scan measurement light on the fundus.

A detection signal (spectral data) from the detector 120 is transmitted to the PC 90 via the USB ports 79*a* and 79*b* (refer to FIG. 6). The PC 90 receives the detection signal, and generates the tomographic image 83 by computationally processing the detection signal.

When the PC 90 generates the tomographic image 83, the PC 90 transmits the tomographic image 83 to the control unit 70 of the device main body 1 via the USB 2.0 ports 78a and 78b and the HUB 71. The control unit 70 receives the tomographic image 83 from the PC 90 via the USB 2.0 ports 78a and 78b and the HUB 71, and displays the tomographic image 83 on the display unit 75. As illustrated in FIG. 3, the control unit 70 displays the anterior chamber observation image 81, the FC front image 82, and the tomographic image 83 on the display unit 75.

The inspector confirms the tomographic image 83 which is being updated real-time, and adjusts an alignment in the Z direction. For example, the alignment may be adjusted in such a manner that the tomographic image 83 is fitted in a display frame.

Naturally, the PC 90 may display the generated tomographic image 83 on the display unit 95. The PC 90 may display the generated tomographic image 83 on the display unit 95 in real time. In addition to the tomographic image 83, the PC 90 may display the anterior chamber observation image 81 and the FC front image 82 on the display unit 95.

In the description, the inspector manually adjusts an image focus by operating an adjustment knob 74d or the like; however, the present invention is not limited to the method given in this embodiment. For example, the inspector may adjust an image by touching the display unit (for example, the display unit 75) having a touch panel function.

When the alignment and the image quality adjustment are completed, the control unit 70 forms an tomographic image by controlling the driving of the scanning unit 108 to scan measurement light on the fundus in a predetermined direction, and acquiring a photodetection signal corresponding to a predetermined scan region from an output signal from the detector 120 during the scanning operation.

FIG. 3 is a view illustrating an example of a display screen displayed on the display unit 75. The control unit 70 displays the anterior chamber observation image 81 acquired by the anterior chamber observation optical system 60, the FC front image 82, and the tomographic image 83, and a line 85 on the display unit 75. The scanning line 85 is an index indicative of a measurement position (an acquisition position) for a tomographic image on the FC front image 82. The scanning line 85 is electrically displayed on the FC front image 82 on the display unit 75.

In the configuration of this example, the inspector can set photographic conditions by performing a touch operation or a drag operation on the display unit 75. The inspector can specify an arbitrary position on the display unit 75 via a touch operation.

<Setting of Scanning Line>

When the tomographic image and the OCT front image 84 are displayed on the display unit 75, the inspector sets a position of a tomographic image to be captured on the OCT front image 84 being observed on the display unit 75 in real time. Here, the inspector sets a scanning position by moving the scanning line 85 with respect to the FC front image 82 (for example, a drag operation of the scanning line SL and an operation of the set display 320). When the line is set in the X direction, a tomographic image in an X-Z plane is captured, and when the scanning line 85 is set in the Y direction, a tomographic image in an Y-Z plane is captured. It may be possible to set the shape of the scanning line 85 to an arbitrary shape (for example, a diagonal line or a circular line).

In this example, the operation of the touch panel display unit 75 provided in the device main body 1 has been described; however, the present invention is not limited to the operation method given in this example. Similar to the display unit 75, it may be possible to operate the joystick 74a or various operation buttons provided in the operation unit 74 of the device main body 1. At this time, for example, an operation signal from the operation unit 74 may be transmitted to the PC via the control unit 70, and the PC may transmit a control signal to the control unit 70 in response to the operation signal.

When the inspector moves the scanning line SL with respect to the FC front image 82, the control unit 70 frequently sets a scanning position, and acquires the corresponding tomographic image at the scanning position. The acquired tomographic image is frequently on a display screen on the display unit 75. The control unit 70 changes a scanning position of the measurement light based on an operation signal from the display unit 75, and displays the scanning line SL at a display position corresponding to the changed scanning position. Since a relationship between the display position (a coordinate position on the display unit) of the scanning line SL and the scanning position of the measurement light by the scanning unit 108 is determined in advance, the control unit 70 properly controls the driving of the two galvanometer mirrors of the scanning unit 108 in such a manner that the measurement light is scanned in a scanning range corresponding to the display position of the scanning line SL which is set.

In this configuration, since the OCT front image 84 and the FC front image 82 are simultaneously displayed in separate display regions, the inspector can performs the adjustment of a scanning position, the adjustment of the position of the fixation lamp, the adjustment of a focus, the control of a polarized wave, or the like using the OCT front image 84, and the inspector can perform the adjustment of alignment, the adjustment of a focus, or the like using the FC front image 82.

At this time, since the OCT front image 84 is a front image formed by scanning light, it is possible to confirm detailed information more than the FC front image (for example, it is easy to confirm a passage state of a blood vessel or an abnormal portion). Accordingly, it is possible to properly adjust the scanning position.

In contrast, a flare may occur in the FC front image 82 due to reflection by the subject's eye. The inspector can capture a flare-reduced fundus front image by moving the photography unit 3 with respect to the subject's eye so as to reduce flaring. Alternatively, the inspector can perform the adjustment of alignment using the optical alignment indexes W1 and W2. In addition, the inspector can performs the adjustment of a focus using the focus indexes S1 and S2.

When only one of the OCT front image 84 and the FC front image 82 is displayed, it is difficult to adjust the coherence optical system 200 and the FC optical system 100. In addition, the optical alignment indexes W1 and W2 and the focus indexes S1 and S2 may be invisible due to the scanning line. As a result, it is difficult to properly the OCT front image 84 and the FC front image 82. In contrast, in the embodiment, since both of the OCT front image 84 and the FC front image 82 are displayed, it is possible to properly adjust both of the OCT front image 84 and the FC front image 82.

<Photographic Operation>

As such, after the setting of the photographic conditions is completed, and when the inspector operates the photography start switch 74c, the control unit 70 starts to capture an image. FIG. 8 is a flowchart illustrating the photographic operation. Hereinafter, the photographic operation will be described with reference to FIG. 8.

First, the control unit 70 acquires the FC front image 82 as a still image (a first FC front image) which is illuminated by the observation light source 11 and captured by the imaging element 38 (S11). The acquired first FC front image (hereinafter, referred to as the first infrared fundus image) is received by the PC 90 via the HUB 71 and the USB 2.0 ports 78*a* and 78*b*, and thereafter is stored in the memory 72.

Subsequently, the control unit 70 acquires a tomographic image (S12). The control unit 70 acquires the tomographic image by performing a B scan based on the set scanning position. The control unit 70 drives the scanning unit 108 to scan measurement light in such a manner that a tomographic fundus image corresponding to the position of the scanning line SL is obtained based on the display position of the scanning line SL set on the OCT front image 84.

The PC 90 generates the tomographic image 83 as a still image based on a detection signal from the detector 120. The PC 90 stores the tomographic image 83 in the memory 72.

When the tomographic image is acquired, the control unit 70 re-acquires the FC front image 82 as a still image (the second FC front image) which is illuminated by the observation light source 11 and captured by the imaging element 38 (S13). The acquired second FC front image (hereinafter, referred to as the second infrared fundus image) is received by the PC 90 via the HUB 71 and the USB 2.0 ports 78*a* and 78*b*, and thereafter is stored in the memory 72.

Subsequently, the control unit 70 proceeds to a step in which a color fundus image is acquired by the fundus camera optical system 100. The control unit 70 retracts the dichroic mirror 24 out of the optical path by driving the insertion and removal mechanism 66, and controls the photography light source 14 to emit light.

The fundus of the subject's eye is illuminated by the visible light emitted from the photography light source 14. The reflected light from the fundus passes through the objective lens 25, the opening of the hole mirror 22, the photographic diaphragm 31, the focusing lens 32, the imaging lens 33, and the dichroic mirror 37, and is imaged on the two-dimensional photodetector 35. The color fundus image captured by the two-dimensional photodetector 35 is received by the PC 90 via the HUB 71 and the USB 2.0 ports 78*a* and 78*b*, and thereafter, the color fundus image is stored in the memory 72.

In the configuration of the embodiment, after the tomographic image is acquired, the second infrared fundus image and the color fundus image are automatically acquired; however, the present invention is not limited to the configuration. For example, after the tomographic image has been captured, and before the second infrared fundus image and the color fundus image are acquired, the inspector may performs a fine adjustment of alignment and a focus. For example, after the tomographic image has been captured, the control unit 70 displays an adjustment screen for performing a fine adjustment of alignment and a focus on the display unit 75. While the inspector observes the FC front image 82 displayed on the display unit 75, the inspector performs a fine adjustment of alignment and a focus so as to be able to capture the color fundus image in a desired state. When the inspector turns on the photography start switch 74*c*, the second infrared fundus image and the color fundus image may be captured. In this case, when the inspector turns on the photography start switch 74*c*, first, the control unit 70 acquires the second infrared fundus image. After the control unit 70 acquires the second infrared fundus image, the control unit 70 acquires the color fundus image.

<Image Analysis Process>

When the acquisition of the tomographic image and the color fundus image is completed in this manner, the control unit 70 matches the tomographic image and the color fundus image. Accordingly, the control unit 70 correlates the tomographic image with the color fundus image in terms of position.

Hereinafter, the image analysis process for correlating the tomographic image with the color fundus image in terms of position will be described. In the embodiment, the control unit 70 correlates the tomographic image with the color fundus image in terms of position using the first infrared fundus image (the first front image) acquired when the tomographic image (the first image) is acquired, and the second infrared fundus image (the second front image) acquired when the color fundus image (the second image) is acquired.

For example, the control unit 70 detects the amount of positional deviation between the first infrared fundus image and the second infrared fundus image which are stored in the memory 72, and correlates the tomographic image 83 with the color fundus image in terms of position.

It is possible to use various image processing techniques (a method of using various correlation functions, a method of using Fourier transform, a method of matching characteristic points) as a technique of detecting the amount of positional deviation between the two images.

For example, it may be possible to adopt a technique of deviating the position of a predetermined reference image (for example, the first infrared fundus image) or a target image (the second infrared fundus image) by one pixel, comparing the reference image with the target image, and then detecting the amount of positional deviation between both data when both data best matches with each other (when there is the highest correlation present between both data). In addition, it may be possible to adopt a technique of extracting common characteristic points from the predetermined reference image and the target image, and detecting the positional deviation of the extracted characteristic points.

A phase-only correlation function may be used as a function for obtaining a positional deviation between the two images. In this case, each image is subjected to Fourier transform, and the phase and the amplitude of each frequency component are obtained. The obtained amplitude component for each frequency component is normalized to the size of one. Subsequently, after a phase difference for each frequency between the two images is calculated, the calculated phase difference is subjected to inverse Fourier transform.

Here, when there is no positional deviation present between the two images, only cosine waves are added, and a peak appears at an origin position (0. 0). When there is a positional deviation between the images, a peak appears at a position corresponding to the positional deviation. The amount of positional deviation between the two images is acquired by obtaining the detection position of the peak. With this technique, it is possible to highly accurately detect the amount of positional deviation between the first infrared fundus image and the second infrared fundus image in a short amount of time.

In the technique adopted in the embodiment, the control unit 70 extracts common characteristic points from the first infrared fundus image and the second infrared fundus image, and detects the amount of positional deviation of the extracted characteristic points.

When the control unit 70 detects the amount of positional deviation, the control unit 70 correlates the tomographic image 83 with the color fundus image in terms of position based on the amount of positional deviation.

Here, since the tomographic image 83 and the first infrared fundus image are acquired at substantially the same time (at completely the same time), it is possible to pixel-to-pixel correlate both data with each other. Since the color fundus image and the second infrared fundus image are acquired at substantially the same time (at completely the same time), it is possible to pixel-to-pixel correlate both data with each other. That is, in the embodiment, the first infrared fundus image is acquired, and the tomographic image 83 is rapidly acquired. In addition, the second infrared fundus image is acquired, and the color fundus image is rapidly acquired. For this reason, there is no nearly positional deviation present among the first infrared fundus image, the second infrared fundus image, and other images (the tomographic image and the color fundus image). For this reason, in other words, it is not necessary to correlate the first infrared fundus image, the second infrared fundus image, and the other images with each other in terms of position, and thereby the amount of positional deviation between the first infrared fundus image and the second infrared fundus image can be applied as the amount of positional deviation between the tomographic image 83 and the color fundus image. For this reason, it is not necessary to perform a positional deviation between the images multiple times, and it is possible to easily and accurately correlate the tomgoraphic image 83 with the color fundus image.

For example, the control unit 70 corrects the display position of the scanning line SL displayed on the color fundus image based on the amount of positional deviation in such a manner that the tomographic image 83 matches with the color fundus image. As described above, since the tomographic image 83 and the first infrared fundus image are acquired at substantially the same time, the tomographic image 83 is correlated with the first infrared fundus image well. That is, the acquisition position (position in which the tomographic image is captured) of the tomographic image 83 is specified on the first infrared fundus image based on the display position of the scanning line SL when the acquisition position of the tomographic image 83 is set on the OCT front image 84. Similarly, the color fundus image is also correlated with the second infrared fundus image. The control unit 70 specifies the acquisition position of the tomographic image 83 on the color fundus image based on the amount of positional deviation obtained as described above. The control unit 70 electrically displays the scanning line SL on the color fundus image based on information regarding the specified acquisition position of the tomographic image 83, the scanning line SL being indicative of a photographic position in which the tomographic image is acquired. As such, the control unit 70 corrects the display position of the scanning line SL to be displayed on the color fundus image on based on the amount of positional deviation. Accordingly, the control unit 70 correlates the tomographic image 83 with the color fundus image in terms of position based on the amount of positional deviation.

When the tomographic image are completely correlated with the color fundus image in terms of position, the control unit 70 transmits the images and a correlation result to the PC 90 via the HUB 71 and the USB 2.0 ports 78a and 78b. The PC 90 displays the images and the correlation result on the display unit 95. Naturally, the PC 90 may display the images and the correlation result on the display unit 75. In addition, the control unit 70 may display the images and the correlation result on the display unit 75.

As such, the tomographic image is not correlated with the color fundus image, and in contrast, the inspector acquires the front images captured by the common type of photography when the tomographic image and the color fundus image are acquired, and correlates the tomographic image with the color fundus image based on the amount of positional deviation between the front images captured by the common type of photography. Accordingly, it is possible to accurately perform a correlation between different images (the tomographic image and the color fundus image). As described above, the inspector can confirm an acquisition position on the fundus on the color fundus image corresponding to the acquired desired fundus tomographic image by correlating the tomographic image with the color fundus image. Accordingly, the inspector can accurately understand a correlation between the color fundus image and the tomographic image which have good resolution and good contrast, and are suitable to find lesions from the entirety of the fundus. As a result, the inspector can perform a useful diagnosis of the subject.

As described above, the control unit 70 acquires a series of images in the sequence of the first front image (for example, the first infrared fundus image), the first image (for example, the tomographic image 83), the second front image (for example, the second infrared front image), and the second image (for example, the color fundus image), and thereby it is possible to easily capture the fundus of the subject's eye by acquiring a series of images in the above-mentioned sequence of image acquisition. That is, when the color fundus image is first captured, the pupil of the subject's eye is contracted, and thereby measurement light for tomographic image photography is unlikely to be incident on the subject's eye, and it is difficult to acquire the tomographic image; however, it is possible to easily acquire the tomographic image and the color fundus image by acquiring a series of images in the above-mentioned sequence of image acquisition.

Also, in a case where the front images for correlation are acquired when the tomographic image and the color fundus image are acquired, even though it takes a certain amount of time to acquire the tomographic image, it is possible to easily and accurately correlate the tomographic image with the color fundus image using the first infrared fundus image acquired when the tomgoraphic image is acquired, and the second infrared fundus image acquired when the color fundus image is acquired.

In addition, in a case where the front images for correlation are acquired when the tomgraphic image and the color fundus image are acquired, and the tomographic image photography is performed multiple times, it is possible to easily and accurately correlate a plurality of tomographic images with the color fundus image without capturing a plurality of color fundus images. For example, the control unit 70 acquires infrared fundus images when a plurality of tomographic images are acquired. The control unit 70 calculates the amount of positional deviation between each of the first infrared fundus images acquired when the plurality of tomographic images are acquired, and the second infrared fundus image acquired when the color fundus image is acquired. The control unit 70 correlates the plurality of tomographic images with one color fundus image based on the amount of positional deviation between each of the infrared fundus images and the second infrared fundus image. Accordingly, it is not necessary to acquire the color fundus image whenever acquiring the tomographic image, and when capturing the color fundus image, it is possible to less frequently illuminate the subject's eye by the visible light, and to reduce a burden on the subject. The plurality of tomographic images may be captured according to the same scanning pattern, or different scanning patterns (for example, a line scan, a cross scan, and a map scan).

In the configuration of the embodiment, the tomographic image 83 is acquired along with the first infrared fundus image, and the color fundus image is acquired along with the second infrared fundus image, and thereby it is not necessary to re-correlate the first infrared fundus image, the second infrared fundus image, and the other images with each other in terms of position; however, the present invention is not limited to the configuration. The control unit 70 may be configured to correlate the first infrared fundus image, the second infrared fundus image, and the other images with each other in terms of position. For example, when the control unit 70 correlates the tomographic image 83 with the first infrared fundus image, the control unit 70 acquires the OCT front image 84 as a still image when the tomographic image 83 is acquired. The control unit 70 detects the amount of positional deviation between the still OCT front image and the first infrared fundus image, and correlates the OCT front image with the first infrared fundus image in terms of position, based on the amount of positional deviation. Accordingly, the inspector can understand that a predetermined portion on the OCT front image is correlated with a position on the first infrared fundus image. That is, it is possible to set the acquisition position of the tomographic image on the first infrared fundus image. For example, when the color fundus image is correlated with the second infrared fundus image, the control unit 70 detects the amount of positional deviation between the color fundus image and the second infrared fundus image, and correlates the color fundus image with the second infrared fundus image in terms of position, based on the amount of positional deviation.

In the embodiment, the tomographic image acquired by the line scan is used as the tomographic image correlated with the color fundus image; however, the present invention is not limited to the tomographic image acquired by the line scan. For example, a three-dimensional tomographic image may be used as the tomographic image. In this case, the three-dimensional tomographic image is correlated with the color fundus image based on the amount of positional deviation between the infrared fundus images. When the inspector selects a desired position on the color fundus image after the photography is completed, the control unit 70 extracts a tomographic image from the three-dimensional tomographic image corresponding to the selected position, and displays the tomographic image on the display unit 75.

With the technology of the embodiment, the tomographic image 83 is correlated with the color fundus image; however, the present invention is not limited to the correlation between the tomographic image 83 and the color fundus image. The technology can be applied to a configuration in which the first image is correlated with the second image. For example, the technology can also be applied to the configuration in which an analysis map acquired by analyzing the tomographic image is correlated with the color fundus image. The technology can also be applied to the configuration in which the tomographic image is correlated with the result of visual field measurement.

In the configuration of the embodiment, two front images (the first infrared fundus image and the second infrared fundus image) are acquired as images used to correlate the tomographic image 83 with the color fundus image, and a correlation between the two front images is performed; however, the present invention is not limited to the configuration. At least two or more front images may be acquired. In a case where the control unit 70 acquires a plurality of front images when the first image is acquired, the control unit 70 may select front images for correlation in the best photographic state from the plurality of front images. An image in the best photographic state implies the fact that the image has good contrast and a high luminance value.

In the configuration of the embodiment, two front images (the first infrared fundus image and the second infrared fundus image) are acquired as images used to correlate one tomographic image 83 with one color fundus image; however, the present invention is not limited to the configuration. The technology of the present invention can be applied to a case in which a plurality of tomographic images are correlated with a plurality of color fundus images. In this case, the control unit 70 acquires a plurality of front images along with a plurality of the first images. The control unit 70 acquires a plurality of front images along with a plurality of the second images. Here, when the control unit 70 selects one tomographic image from the plurality of tomographic images, and correlates the tomographic image with the color fundus images, the control unit 70 sequentially calculates the amount of positional deviation between the selected front tomographic image and the front images of the plurality of color fundus images. The control unit 70 may select a color fundus image from the plurality of color fundus images, which is correlated with a front image having the smallest amount of positional deviation among the calculated amount of positional deviation, and correlate the selected color fundus image with the selected tomographic image. For example, when the control unit 70 selects one tomographic image from the plurality of tomographic images, and correlates the tomographic image with the color fundus images, the control unit 70 compares the photographic conditions (for example, the amount of light and a fixation position) of the selected front tomographic image with those of the front images of the plurality of color fundus images. The control unit 70 may select a color fundus image from the plurality of color fundus images, which is correlated with a front image having the most similar photographic conditions, and correlate the selected color fundus image with the selected tomographic image. In the above-mentioned configuration, the control unit 70 selects one tomographic image from the plurality of tomographic images, and correlates the tomographic image with the color fundus image; however, the present invention is not limited to the configuration. For example, the control unit 70 may be configured to correlate one selected tomographic image with a plurality of color fundus images, or may be configured to correlate a plurality of tomographic images with one selected color fundus image. In this configuration, it is possible to perform a correlation between the first image and the second image which have a close correlation.

The embodiment may have a configuration in which the blinking of the subject's eye is detected by comparing the first front image (for example, the first infrared fundus image) and the second front image (for example, the second infrared fundus image) which are used as references for correlation between different images. For example, the control unit 70 determines whether the subject's eye is blinked by detecting the amount of positional deviation between the first infrared fundus image and the second infrared fundus image stored in the memory 72, and determining whether the amount of positional deviation is greater than a predetermined threshold value. For example, when the amount of positional deviation is greater than the threshold value, the control unit 70 may determine that the subject's eye may be blinked. That is, when the subject's eye is blinked, a common area between the front images is reduced, and the amount of positional deviation is increased. Accordingly, it is possible to detect the blinking of the subject's eye. The present invention is not limited to a configuration in which the blinking of the subject's eye is detected based on the amount of positional deviation between the first infrared fundus image and the second infrared fundus image. The blinking of the subject's eye is preferably detected based on a result of comparison between the first infrared fundus image and the second infrared fundus image which are used as references for correlation. For example, the blinking of the subject's eye may be detected based on whether the similarity between the first front image and the second front image is great. In this case, the control unit 70 may determine whether the first front image and the second front image are similar to each other by comparing a luminance value, contrast, and the like between the first front image and the second front image, and determining the level of a correlation. Accordingly, the control unit 70 determines that the subject's eye is blinked when the similarity between the images is low. As such, since the embodiment has the configuration in which the blinking of the subject's eye is detected by comparing the first front image acquired when the first image (for example, the tomographic image) is acquired with the second front image after the acquisition of the first image is completed, and thereby it is possible to detect whether the subject's eye is blinked during the photography of the first image. For this reason, it is possible to acquire a good first image.

In the embodiment, the amount of positional deviation may be detected except for that of a predetermined region. For example, when the control unit 70 detects the amount of positional deviation between the first front image and the second front image, the control unit 70 detects the amount of positional deviation except for a predetermined region on each of the first front image and the second front image. That is, the control unit 70 excludes potentially problematic portions from a region in which the amount of positional deviation is detected. For example, the control unit 70 sets a predetermined region (for example, a region for a slit index or a region for a working dot) on each of the first infrared fundus image and the second infrared fundus image, and detects the amount of positional deviation in a state where the predetermined regions are excluded from the computation of the amount of positional deviation. The predetermined regions may be excluded based on photographic conditions (for example, a scanning patter and fixation position). As such, it is possible to accurately calculate the amount of positional deviation by calculating the amount of positional deviation in a state where the region for the split index or the working dot is superimposed on the fundus in the front images for correlation. Accordingly, it is possible to accurately correlate the first image with the second image. It is possible to set the excluded predetermined region by specifying the problematic portions on front images for correlation obtained by capturing a schematic eye, and storing a coordinate position corresponding to the region in the memory 72. Naturally, the excluded predetermined region may be set by detecting the problematic region from the captured front images for correlation.

In the configuration of the ophthalmic capture device of the embodiment, the fundus of the subject's eye is captured; however, the present invention is not limited to the configuration. The technology can be applied to a case in which the anterior chamber of the subject's eye is captured.

DESCRIPTION OF REFERENCE NUMERALS AND SIGNS

1: ophthalmic photography device
70: control unit
71: HUB
74: operation unit
75: display unit
76, 77: USB signal line
78a, 78b: USB 2.0 port
79a, 79b: USB port
90: computer
95: display unit

What is claimed is:

1. An ophthalmic photography device for capturing a subject's eye, the device comprising:
 a first photography optical system configured to capture a first image of the subject's eye by performing a first type of photography;
 a second photography optical system configured to capture a second image of the subject's eye by performing a second type of photography that is different from the first type of photography;
 a third photography optical system configured to capture a front image of the subject's eye by performing a third type of photography that is different from the first and second types of photography; and
 a controller configured to: (i) control the third photography optical system to capture a first front image when the first image is captured by the first photography optical system, and to capture a second front image different from the first front image when the second image is captured by the second photography optical system, (ii) detect an amount of positional deviation between the first front image and the second front image, and (iii) associate the first image with the second image based on the amount of positional deviation.

2. The ophthalmic photography device according to claim 1, wherein
 the third photography optical system includes an infrared illumination optical system configured to illuminate a fundus of the subject's eye by an infrared light, and an infrared photography optical system configured to capture the first front image and the second front image of the fundus illuminated by the infrared light.

3. The ophthalmic photography device according to claim 2, wherein
 the first photography optical system includes an Optical Coherence Tomography (OCT) optical system configured to capture a tomographic image of the fundus as the first image using optical coherence tomography, and
 the second photography optical system includes a visible light illumination optical system configured to illuminate the fundus of the subject's eye by visible light, and a visible light photography optical system configured to capture a color fundus image of the fundus illuminated by the visible light as the second image.

4. The ophthalmic photography device according to claim 3, wherein
 the controller specifies a capture position of the tomographic image captured by the first photography optical system relative to the color fundus image captured by the second photography optical system by associating the tomographic image with the color fundus image, and the controller superimposes a mark on the color fundus image based on the specified capture position, the mark being indicative of the capture position at which the tomographic image is captured.

5. The ophthalmic photography device according to claim 1, further comprising:

a detector configured to detect a blinking of the subject's eye by comparing the first front image with the second front image.

6. The ophthalmic photography device according to claim 1, wherein the controller detects the amount of positional deviation except at a predetermined region on each of the first front image and the second front image.

7. The ophthalmic photography device according to claim 1, wherein the controller controls the third photography optical system to capture the first front image, controls the first photography optical system to capture the first image after the first front image has been captured, controls the third photography optical system to capture the second front image after the first image has been captured, and controls the second photography optical system to capture the second image after the second front image has been captured.

8. The ophthalmic photography device according to claim 1, wherein the first photography optical system is an Optical Coherence Tomography (OCT) optical system, and the second photography optical system is a fundus camera optical system.

9. An ophthalmic image processing method comprising:

capturing a first image of a subject's eye by performing a first type of photography;

capturing a second image of the subject's eye by performing a second type of photography that is different from the first type of photography;

capturing a front image of the subject's eye by performing a third type of photography that is different from the first and second types of photography, the capturing of the front image including capturing a first front image with the third type of photography when the first image is captured, and capturing a second front image with the third type of photography when the second image is captured, the second front image being different from the first front image; and detecting an amount of positional deviation between the first front image and the second front image, and associating the first image with the second image based on the amount of positional deviation.

10. The method according to claim 9, wherein:

the first image is captured by a first photography optical system configured to capture the first image of the subject's eye by performing the first type of photography, the second image is captured by a second photography optical system configured to capture the second image of the subject's eye by performing the second type of photography, and the first and second front images are captured by a third photography optical system configured to capture the third image of the subject's eye by performing the third type of photography.

11. The method according to claim 10, wherein the first, second and third photography optical systems are included in an ophthalmic photography device.

12. A non-transitory computer-readable storage medium on which is stored an ophthalmic photography program that, when executed by a control device configured to control an operation of an ophthalmic photography device that captures a subject's eye, causes the control device to control the ophthalmic photography device to execute the following steps:

capturing a first image of the subject's eye by performing a first type of photography;

capturing a second image of the subject's eye by performing a second type of photography that is different from the first type of photography;

capturing a front image of the subject's eye by performing a third type of photography that is different from the first and second types of photography, the capturing of the front image including capturing a first front image with the third type of photography when the first image is captured, and capturing a second front image with the third type of photography when the second image is captured, the second front image being different from the first front image; and detecting an amount of positional deviation between the first front image and the second front image, and associating the first image with the second image based on the amount of positional deviation.

* * * * *